(12) United States Patent
Kim et al.

(10) Patent No.: US 12,109,300 B2
(45) Date of Patent: Oct. 8, 2024

(54) METHOD FOR PREPARING ENZYME-TREATED ZIZANIA LATIFOLIA TURCZ. EXTRACT HAVING INCREASED TRICIN CONTENT, AND COMPOSITION FOR WHITENING, WRINKLE REDUCTION, ANTI-INFLAMMATION, ANTI-ALLERGY AND MOISTURIZATION, PREPARED THEREBY

(71) Applicant: BTC CORPORATION, Ansan-si (KR)

(72) Inventors: Tae Young Kim, Ansan-si (KR); Joo Myung Moon, Ansan-si (KR); Sung Kwan Jo, Seoul (KR)

(73) Assignee: BTC CORPORATION, Ansan-si (KR)

( * ) Notice: Subject to any disclaimer, the term of this patent is extended or adjusted under 35 U.S.C. 154(b) by 943 days.

(21) Appl. No.: 17/049,025

(22) PCT Filed: Sep. 3, 2019

(86) PCT No.: PCT/KR2019/011352
§ 371 (c)(1),
(2) Date: Oct. 19, 2020

(87) PCT Pub. No.: WO2020/122360
PCT Pub. Date: Jun. 18, 2020

(65) Prior Publication Data
US 2021/0251883 A1 Aug. 19, 2021

(30) Foreign Application Priority Data
Dec. 12, 2018 (KR) .................. 10-2018-0160061

(51) Int. Cl.
| | | |
|---|---|---|
| A61K 36/00 | (2006.01) |
| A23L 29/00 | (2016.01) |
| A23L 33/00 | (2016.01) |
| A23L 33/105 | (2016.01) |
| A61K 8/49 | (2006.01) |
| A61K 8/9794 | (2017.01) |
| A61K 31/353 | (2006.01) |
| A61K 36/899 | (2006.01) |
| A61P 29/00 | (2006.01) |
| A61P 37/08 | (2006.01) |
| A61Q 19/02 | (2006.01) |
| A61Q 19/08 | (2006.01) |

(52) U.S. Cl.
CPC ............ *A61K 8/9794* (2017.08); *A23L 29/06* (2016.08); *A23L 33/105* (2016.08); *A23L 33/40* (2016.08); *A61K 8/498* (2013.01); *A61K 31/353* (2013.01); *A61K 36/899* (2013.01); *A61P 29/00* (2018.01); *A61P 37/08* (2018.01); *A61Q 19/02* (2013.01); *A61Q 19/08* (2013.01); *A23V 2002/00* (2013.01); *A61K 2236/19* (2013.01); *A61K 2236/333* (2013.01); *A61K 2800/805* (2013.01)

(58) Field of Classification Search
None
See application file for complete search history.

(56) References Cited

FOREIGN PATENT DOCUMENTS

| | | | |
|---|---|---|---|
| KR | 10-2006-0123886 A | 12/2006 |
| KR | 10-2009-0127970 A | 12/2009 |
| KR | 10-2010-0104334 A | 9/2010 |
| KR | 10-1181321 B1 | 9/2012 |
| KR | 10-2015-0090954 A | 8/2015 |
| KR | 10-2018-0063397 A | 6/2018 |

OTHER PUBLICATIONS

International Search Report for PCT/KR2019/011352 mailed Dec. 6, 2019 from Korean Intellectual Property Office.
Moon, J.-M. et al., "Protection against UVB-InducedWrinkle Formation in SKH-1 Hairless Mice: Efficacy of Tricin Isolated from Enzyme-Treated Zizania latifolia Extract", Molecules Sep. 4, 2018, vol. 23, article No. 2254 (pp. 1-12).

*Primary Examiner* — Russell G Fiebig
(74) *Attorney, Agent, or Firm* — Revolution IP, PLLC

(57) ABSTRACT

The present invention relates to a method of preparing an enzyme-treated Zizania *latifolia* Turcz. extract and a composition prepared therefrom, and the enzyme-treated Zizania *latifolia* Turcz. extract prepared by the above method contains a high content of tricin, and thus it can be usefully used as a cosmetic composition or a health functional food composition for whitening, wrinkle improvement, anti-inflammatory, anti-allergy and moisturizing.

4 Claims, 24 Drawing Sheets

[FIG. 1]
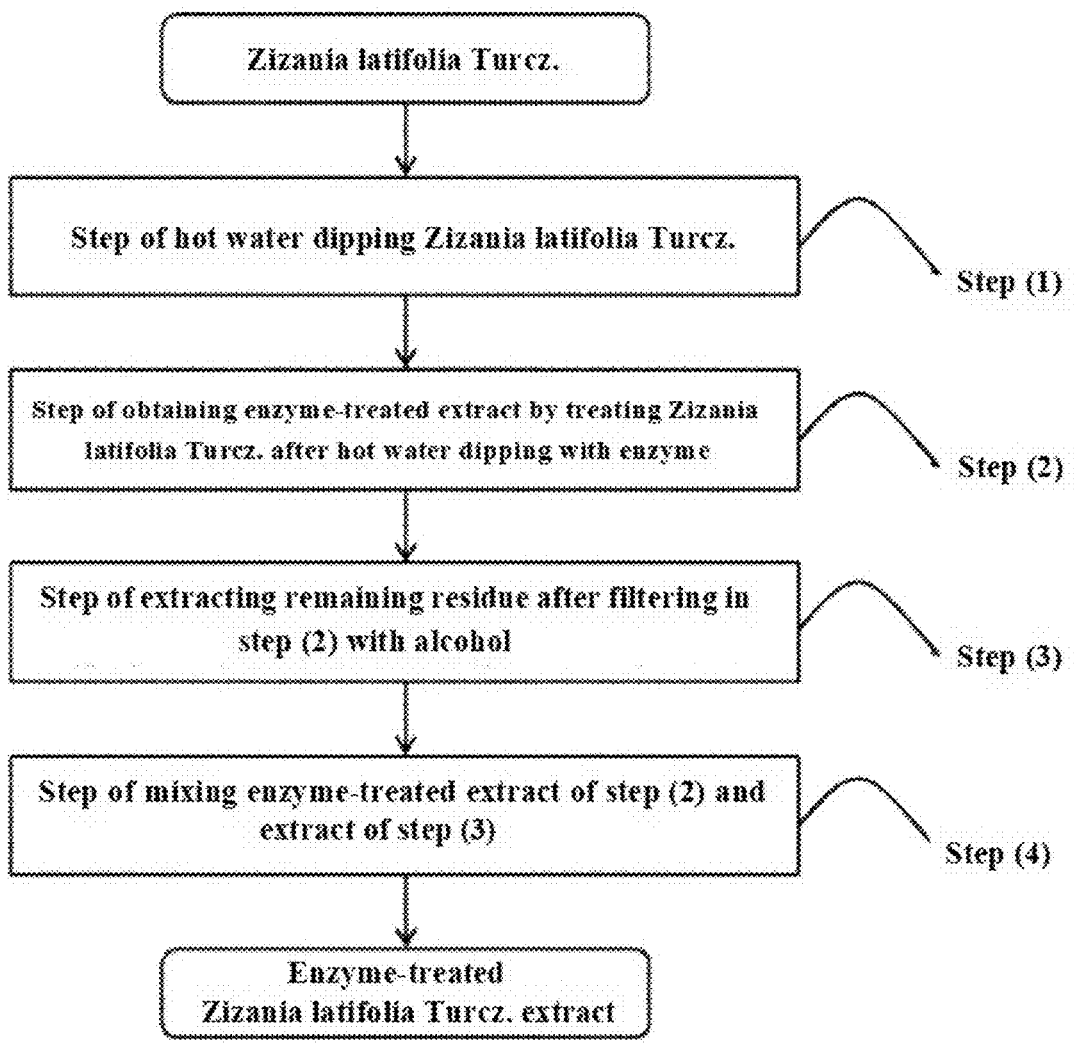

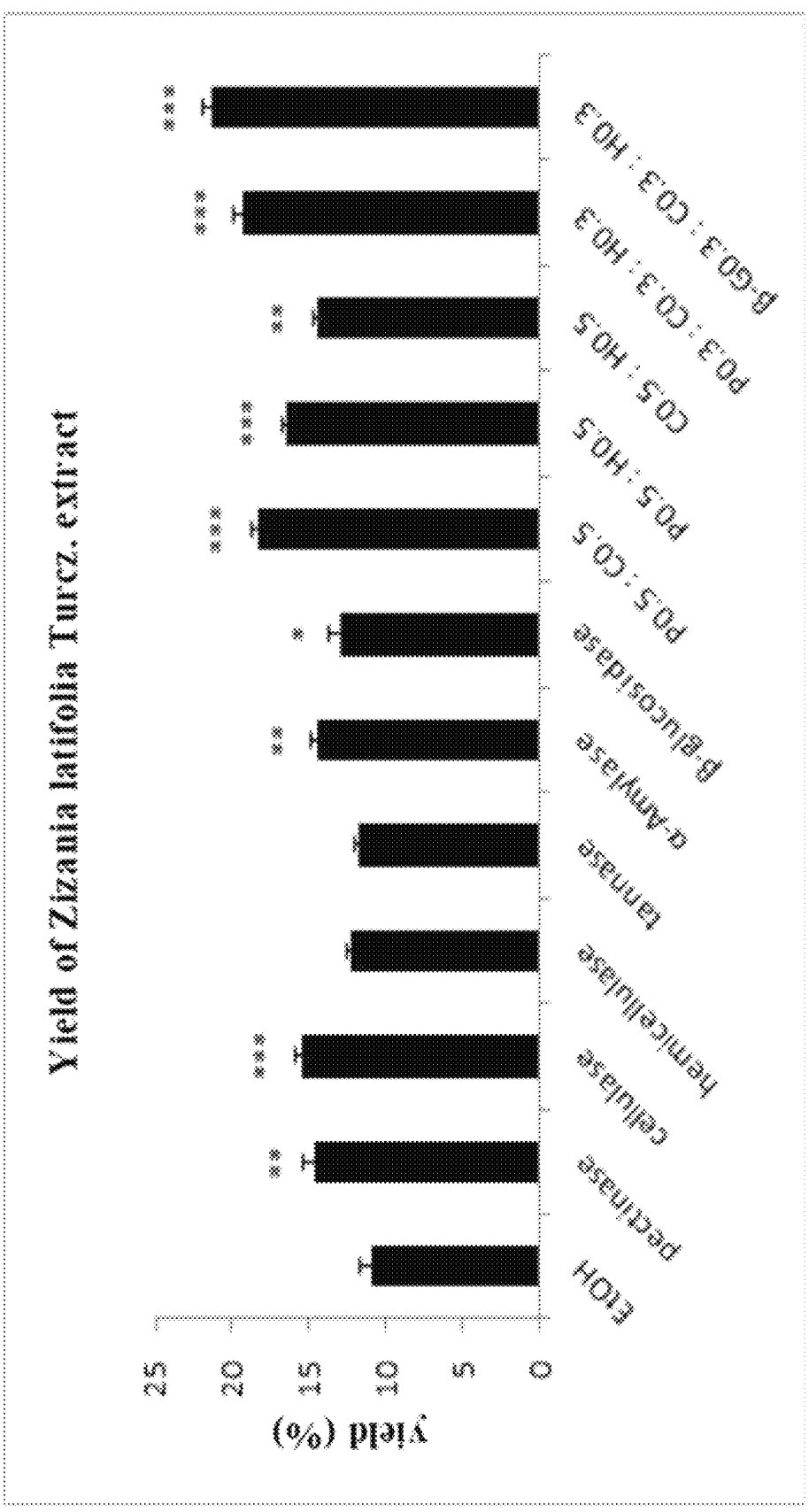
[FIG. 2]

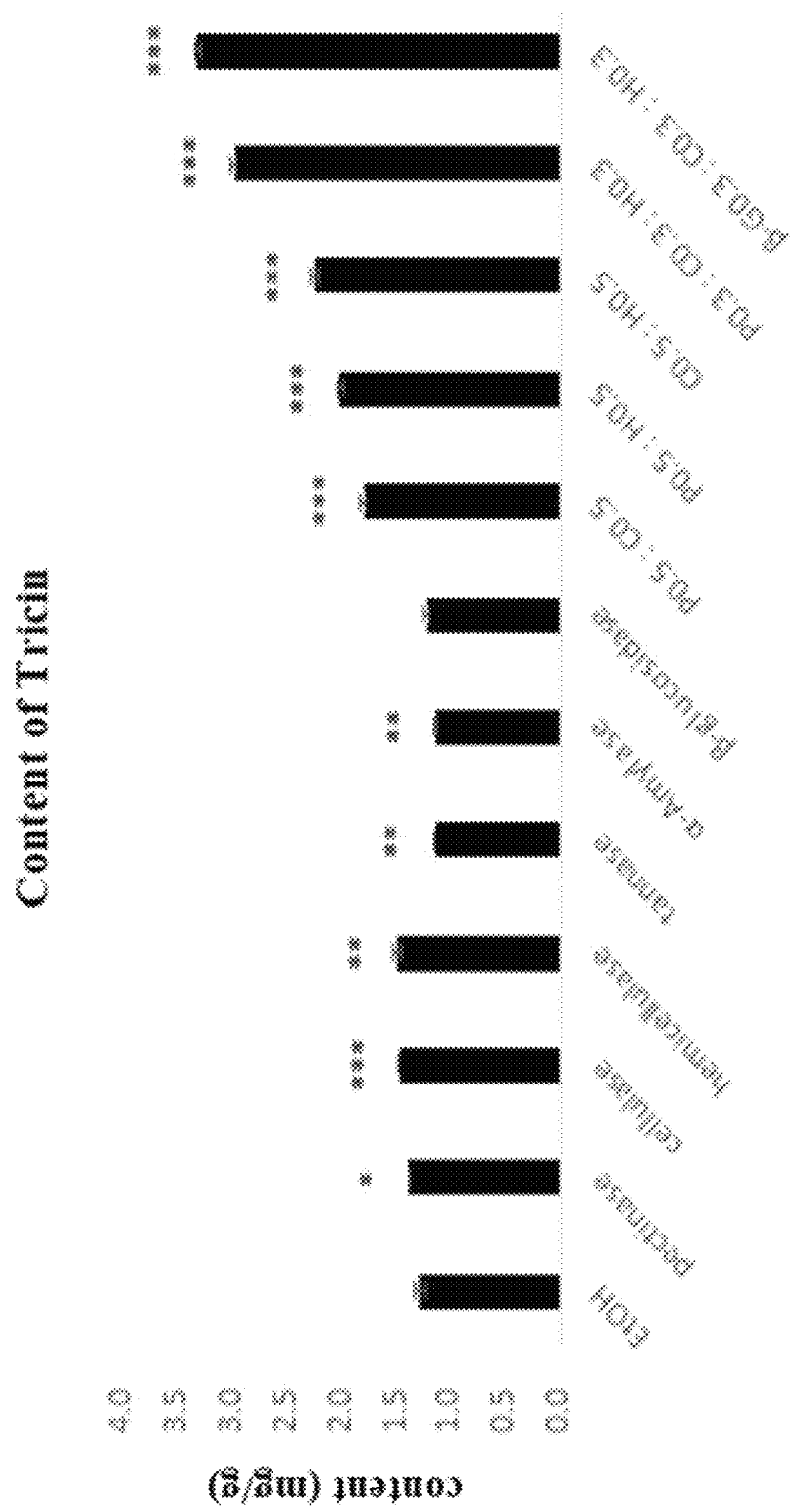
[FIG. 3]

[FIG. 4]
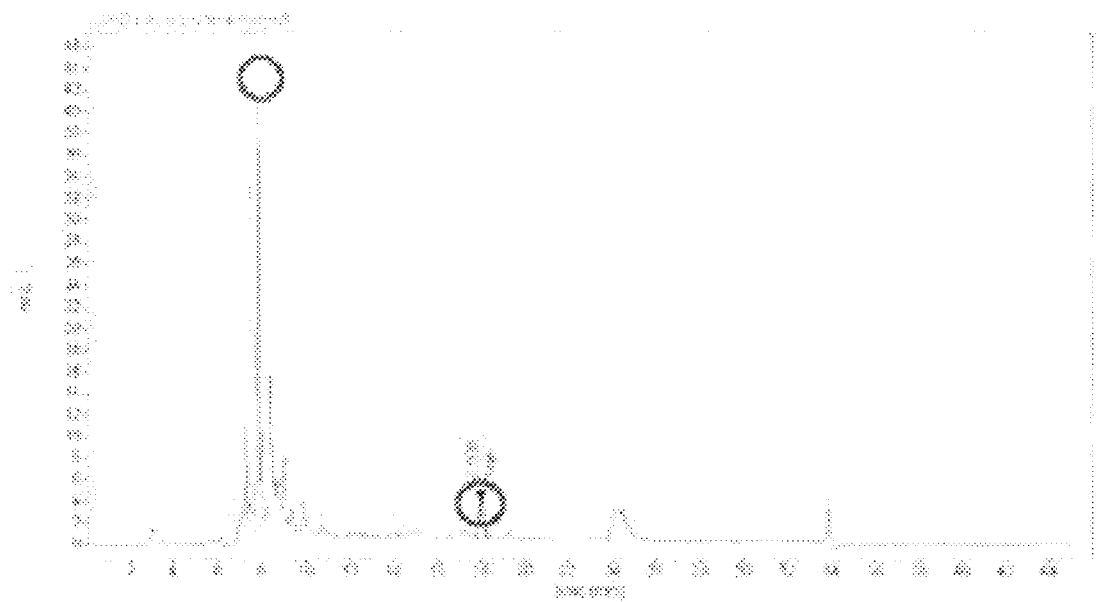
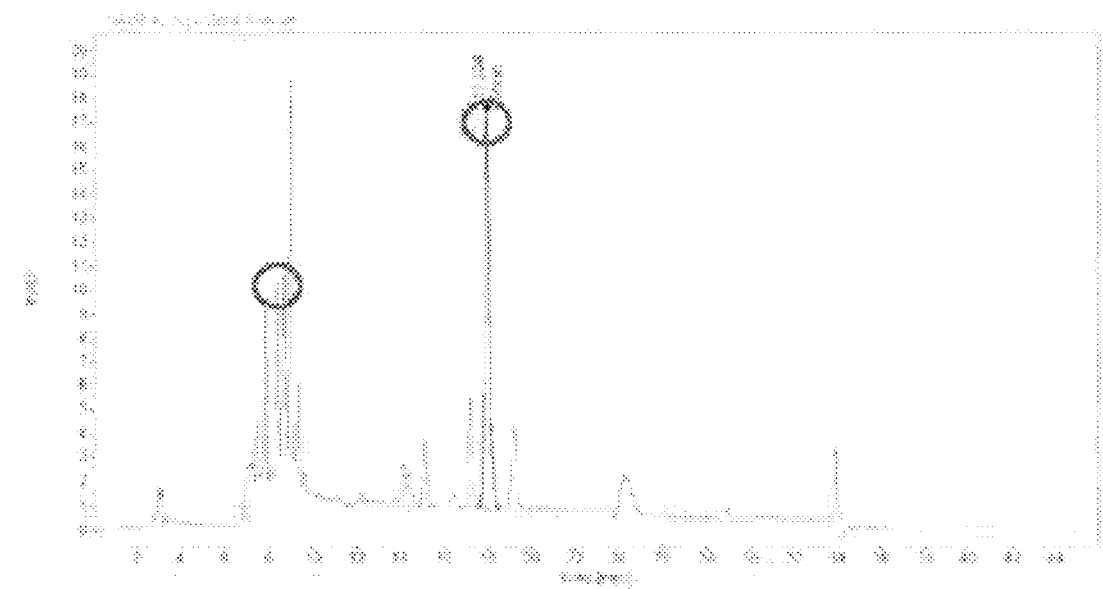

[FIG. 5]
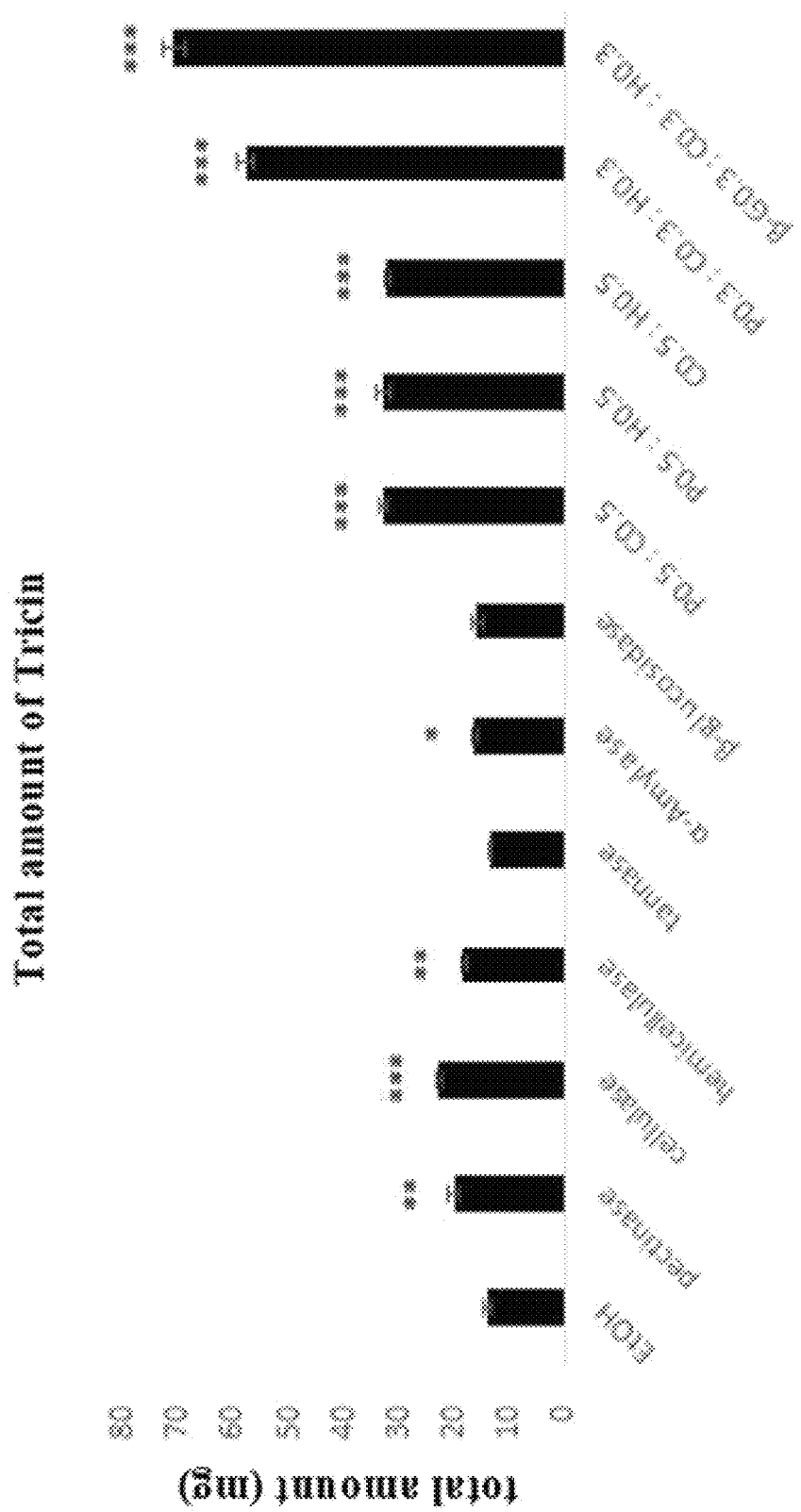

[FIG. 6]
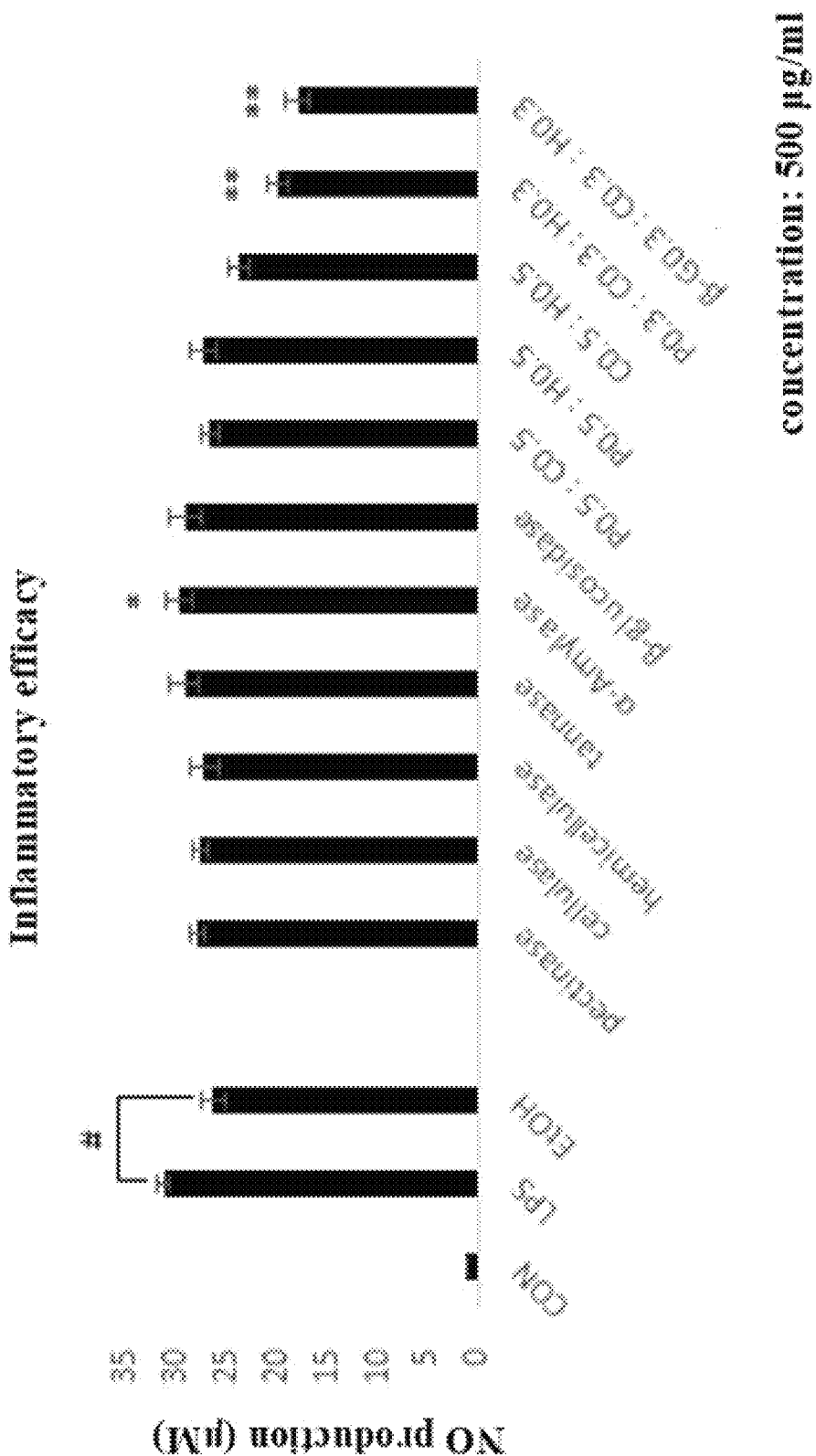

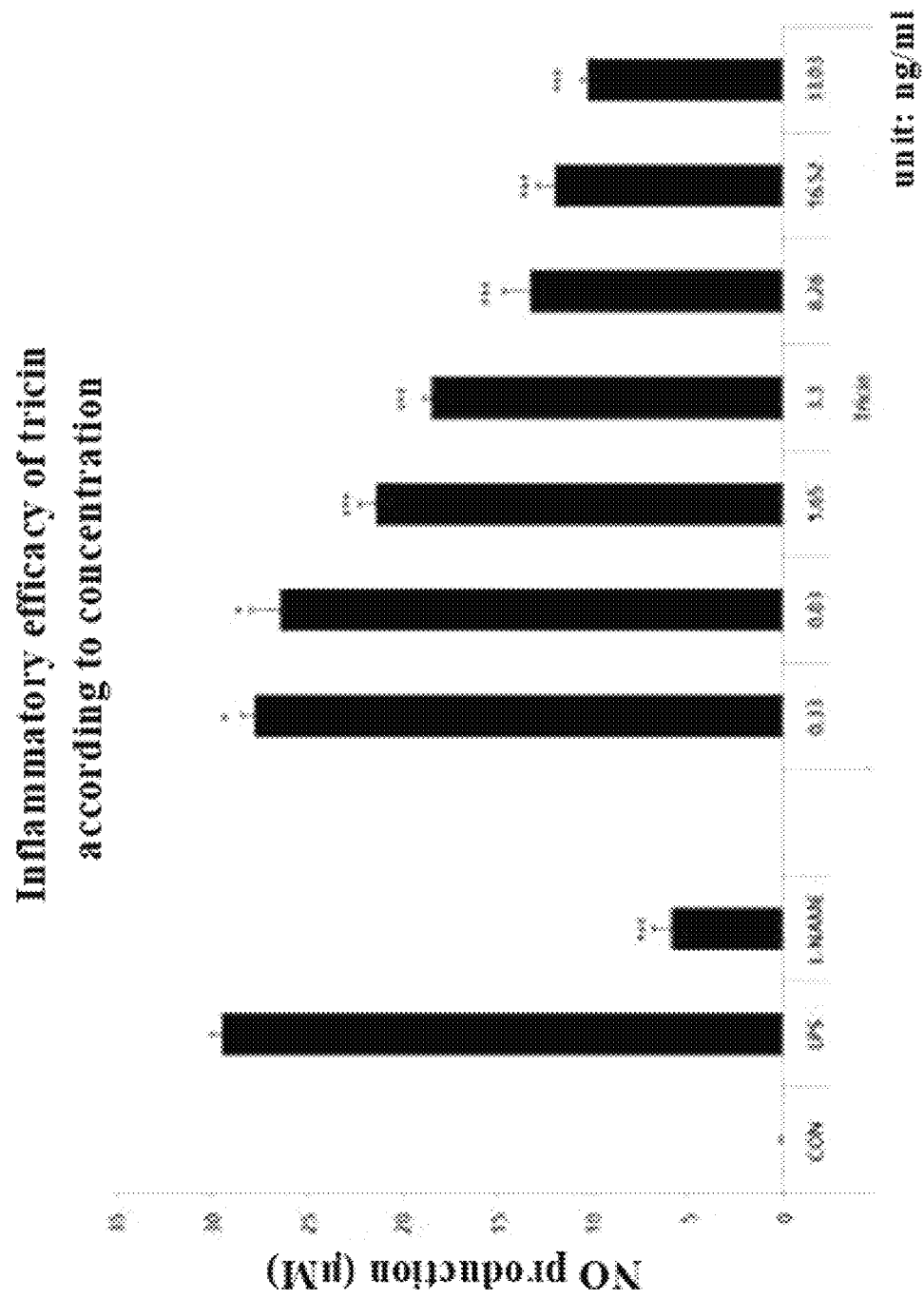
[FIG. 7]

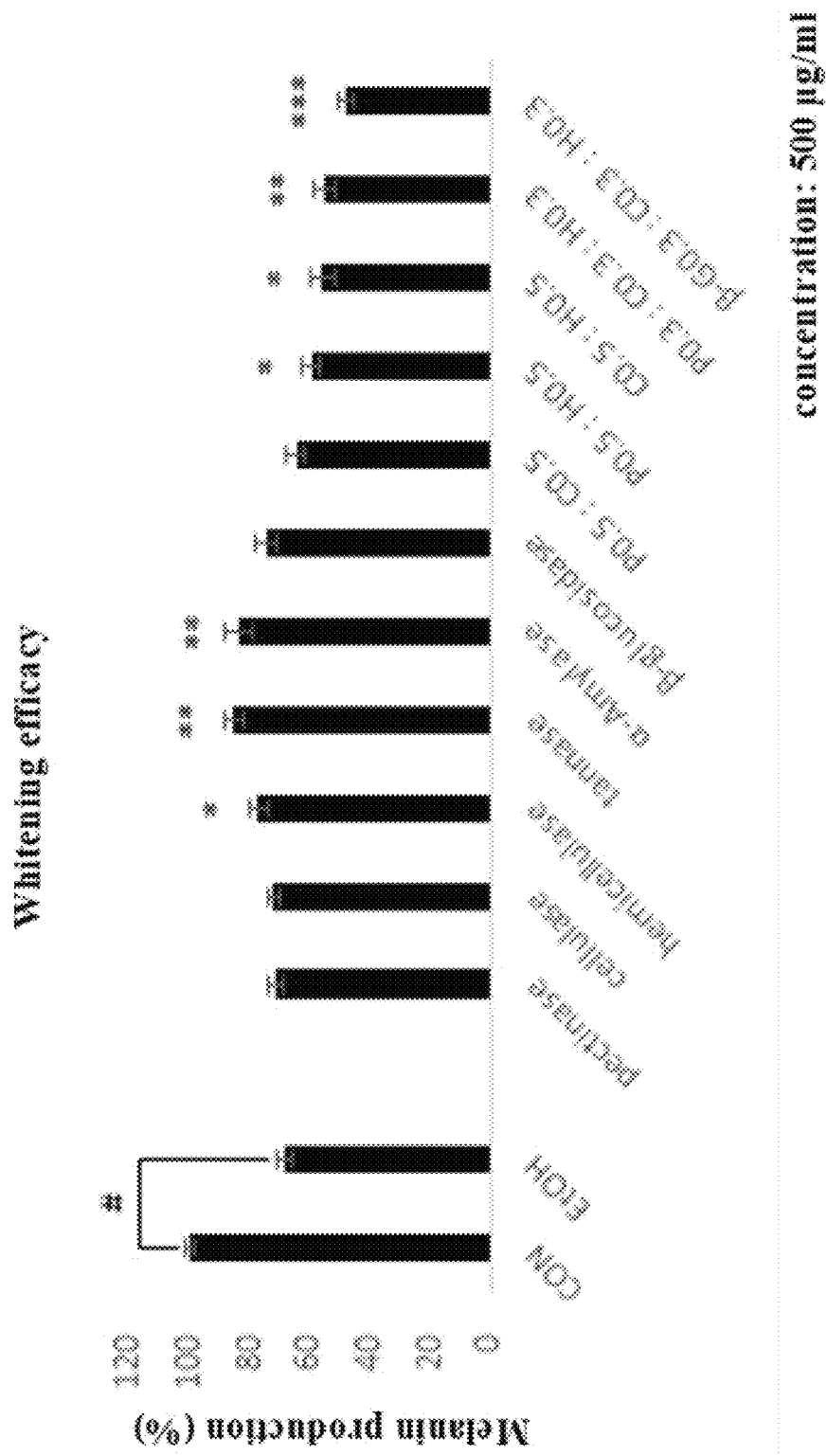
[FIG. 8]

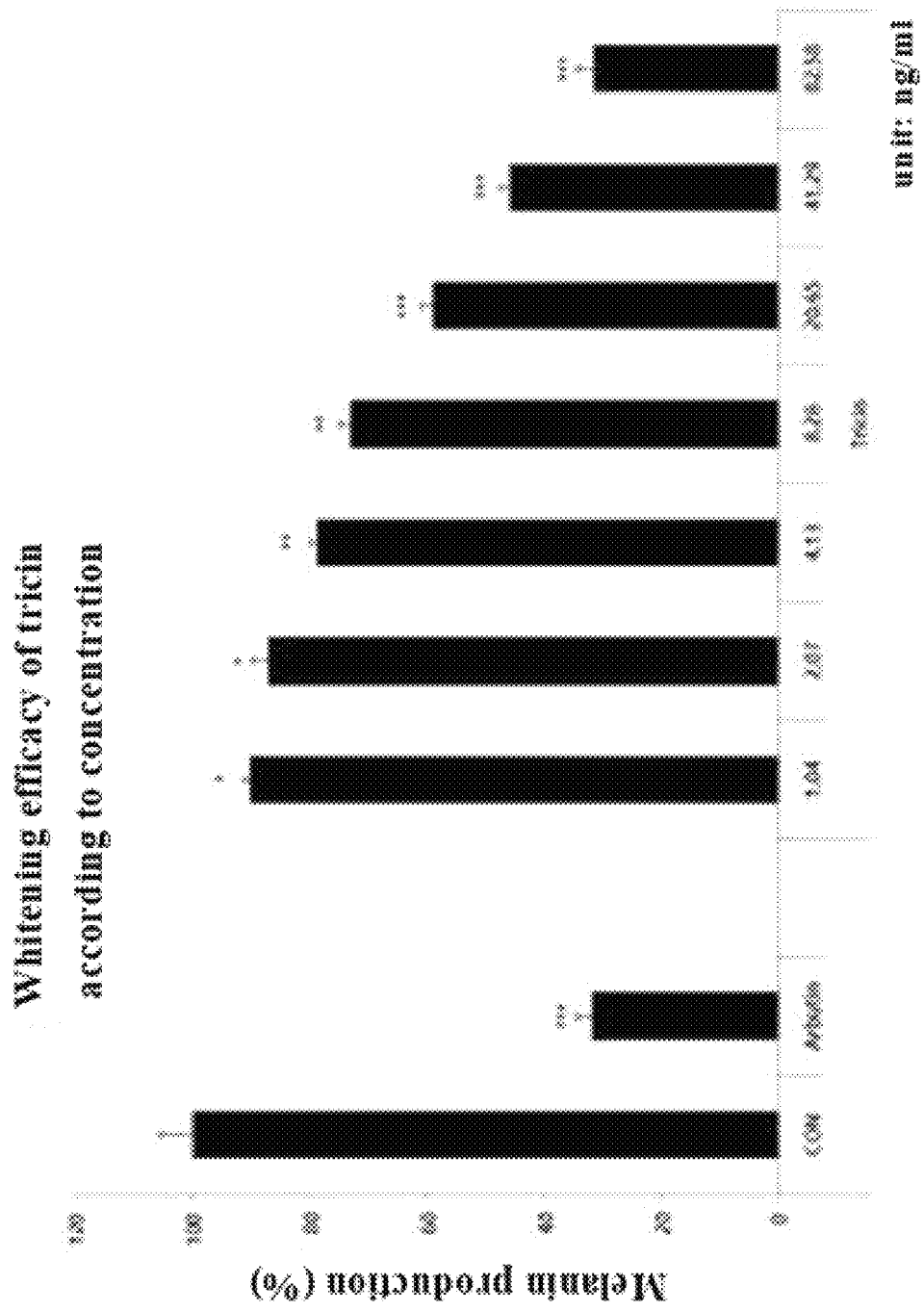
[FIG. 9]

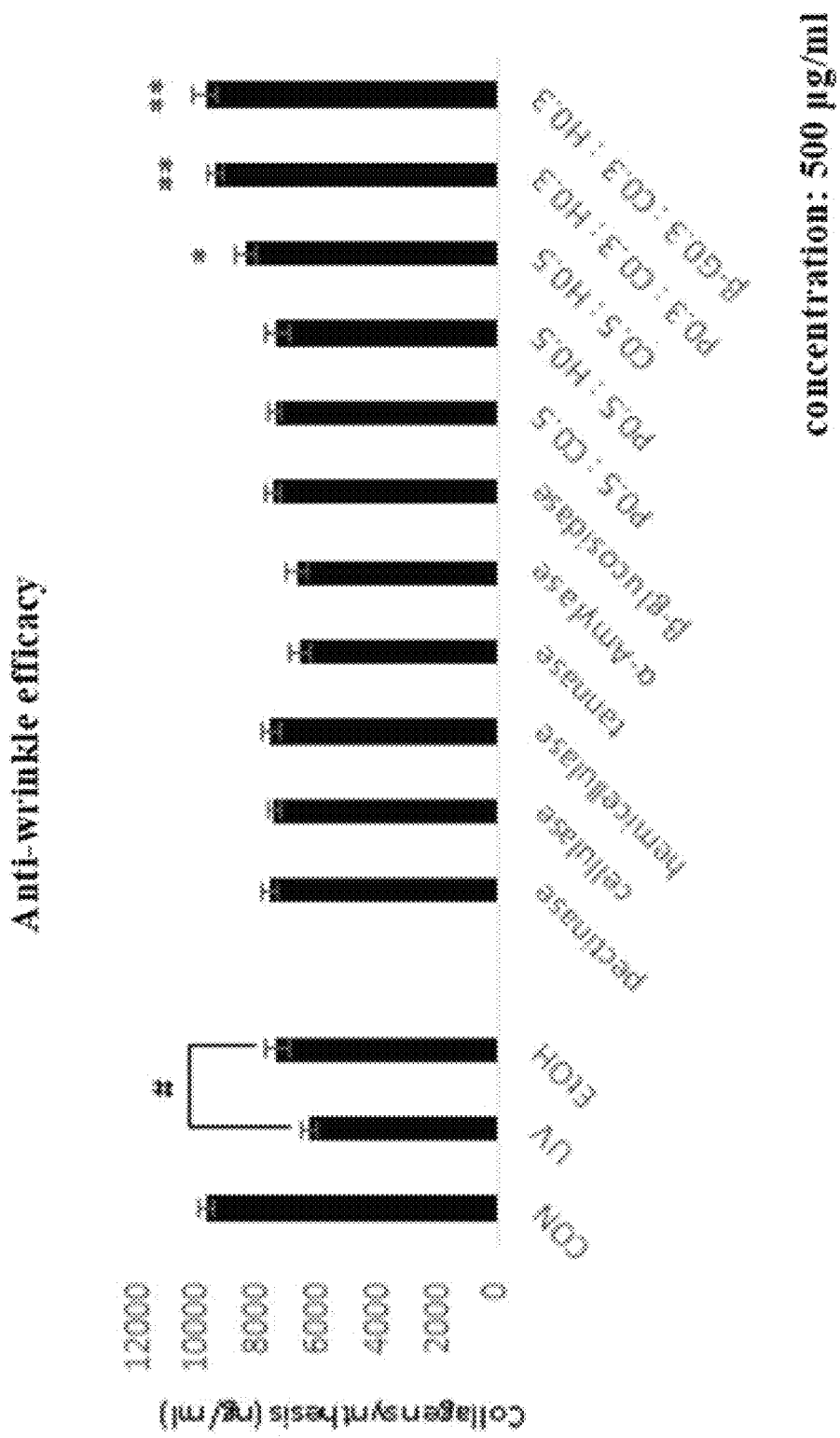
[FIG. 10]

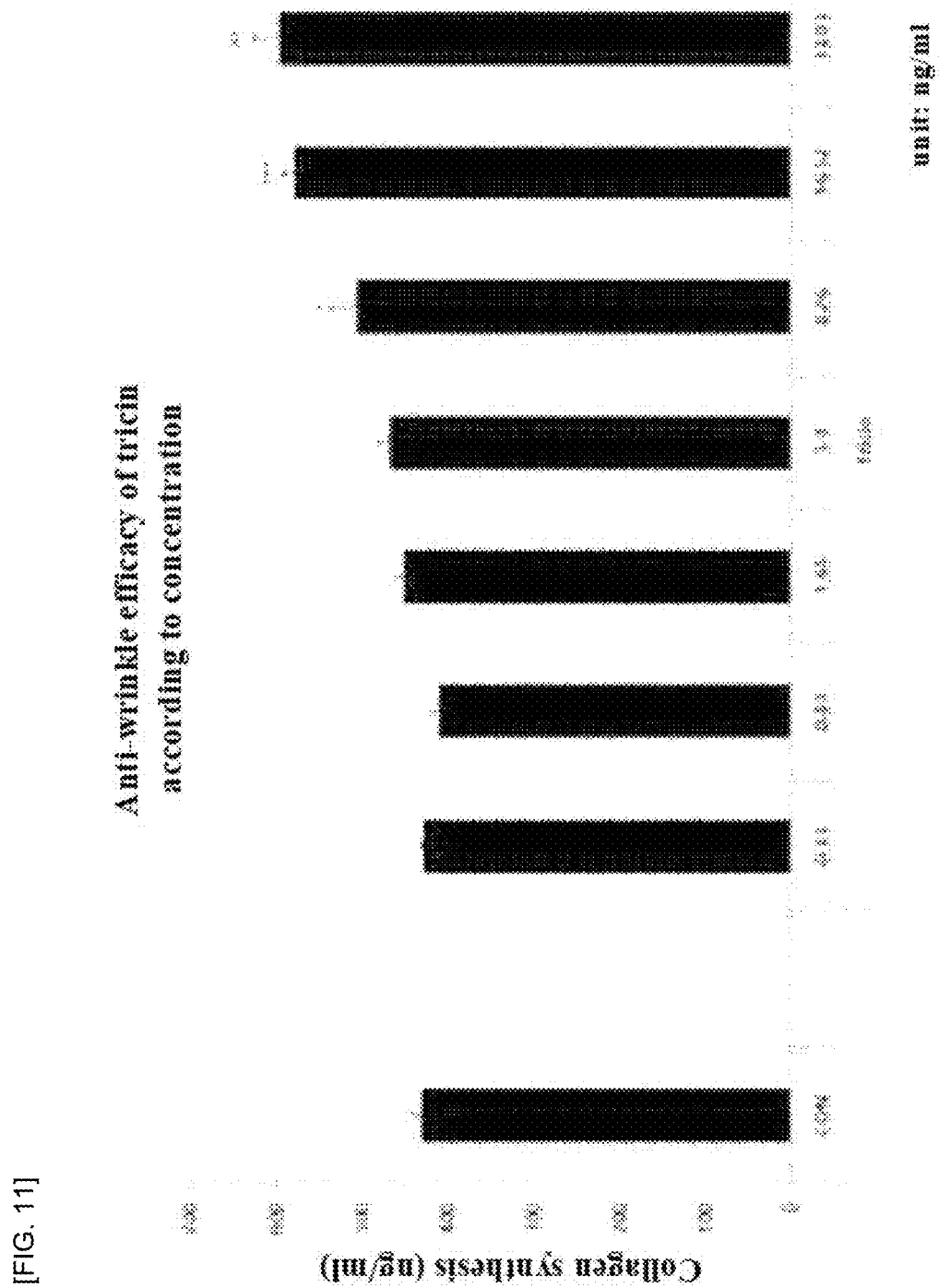
[FIG. 11]

[FIG. 12]
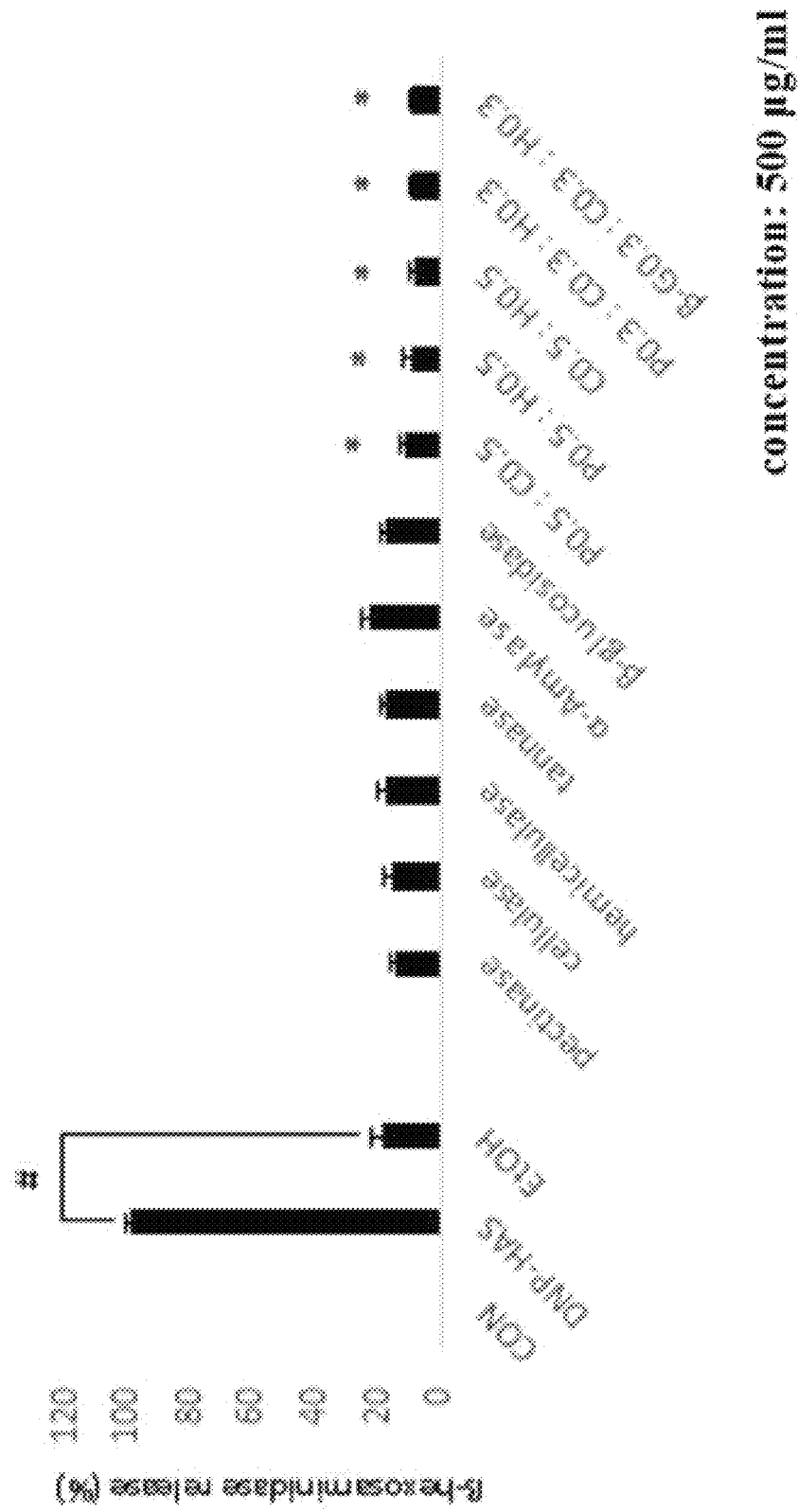

[FIG. 13]
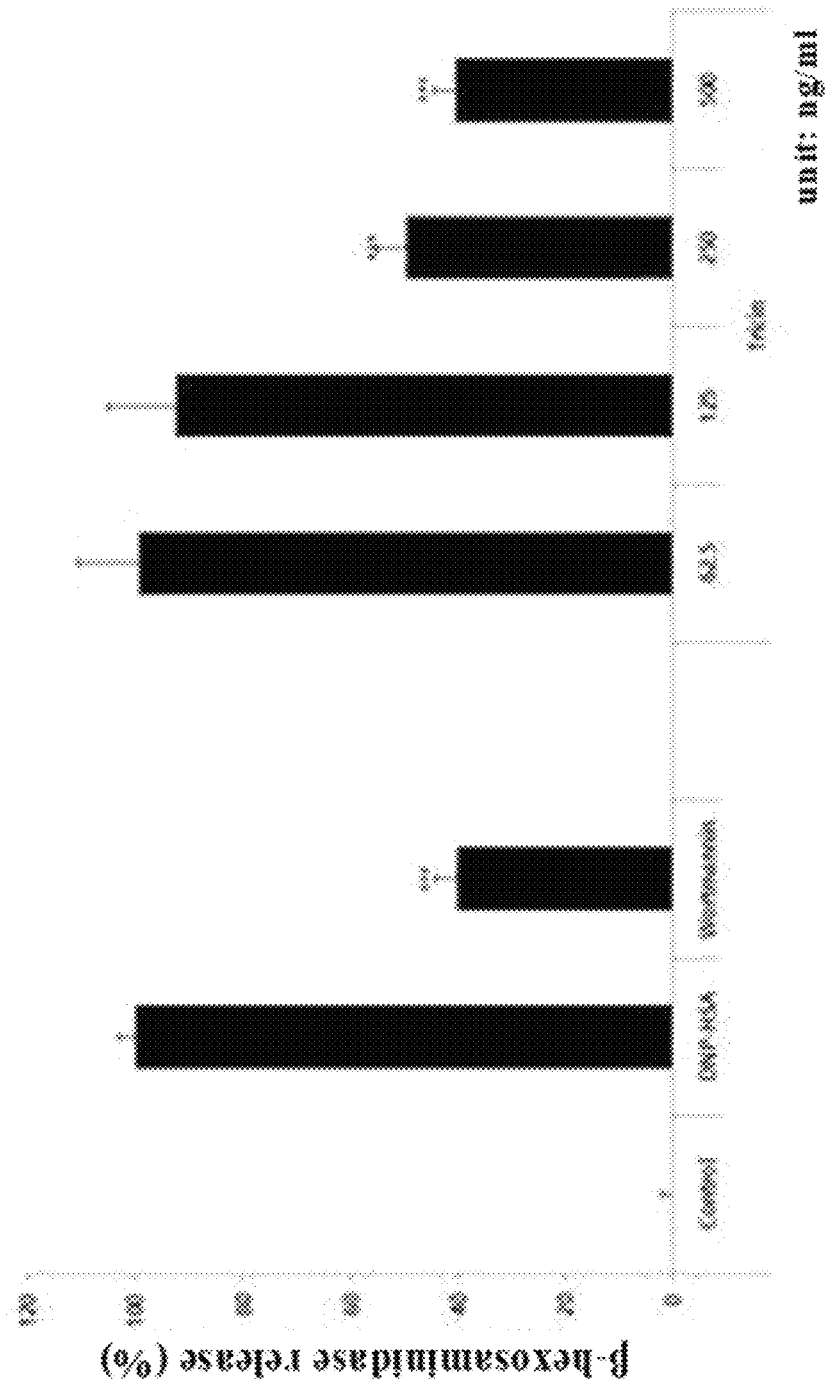

[FIG. 14]
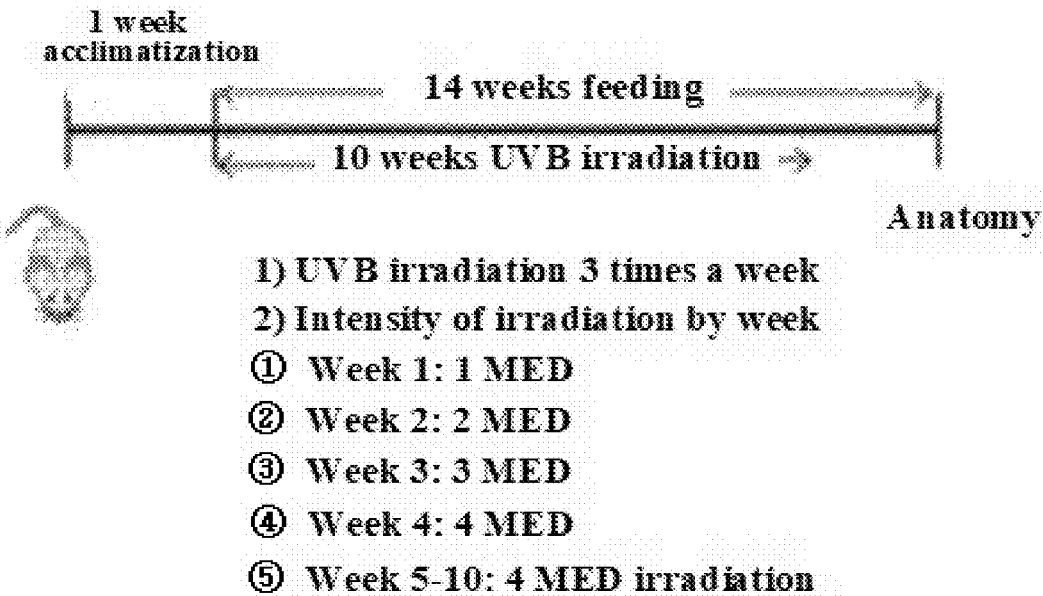
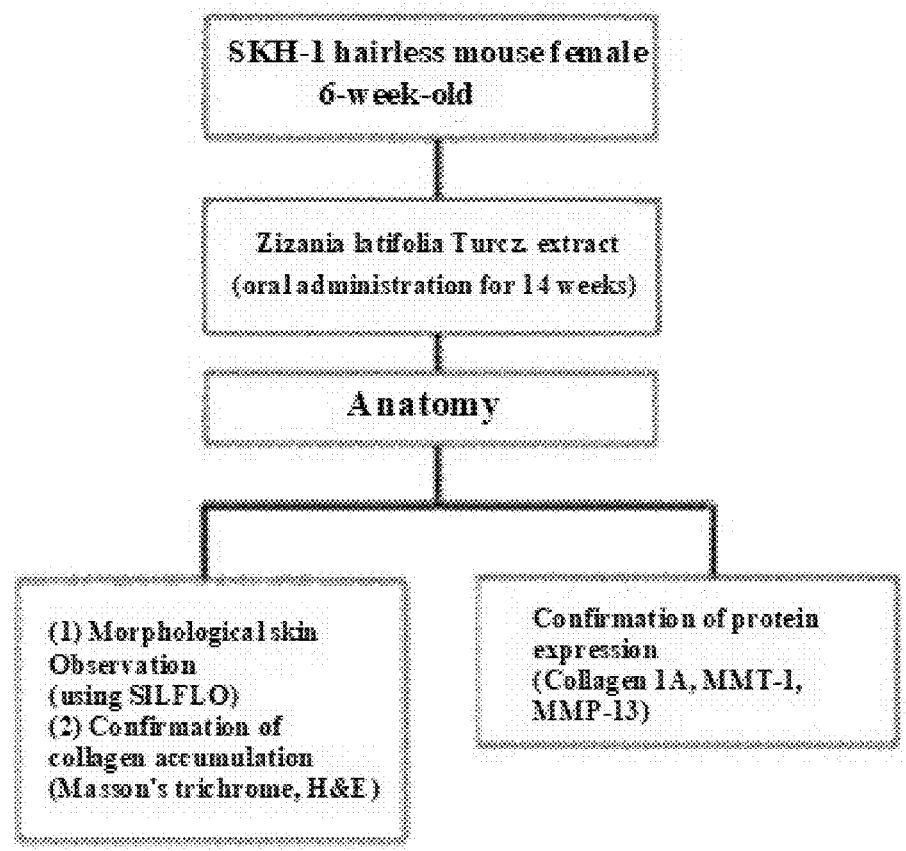

[FIG. 15]
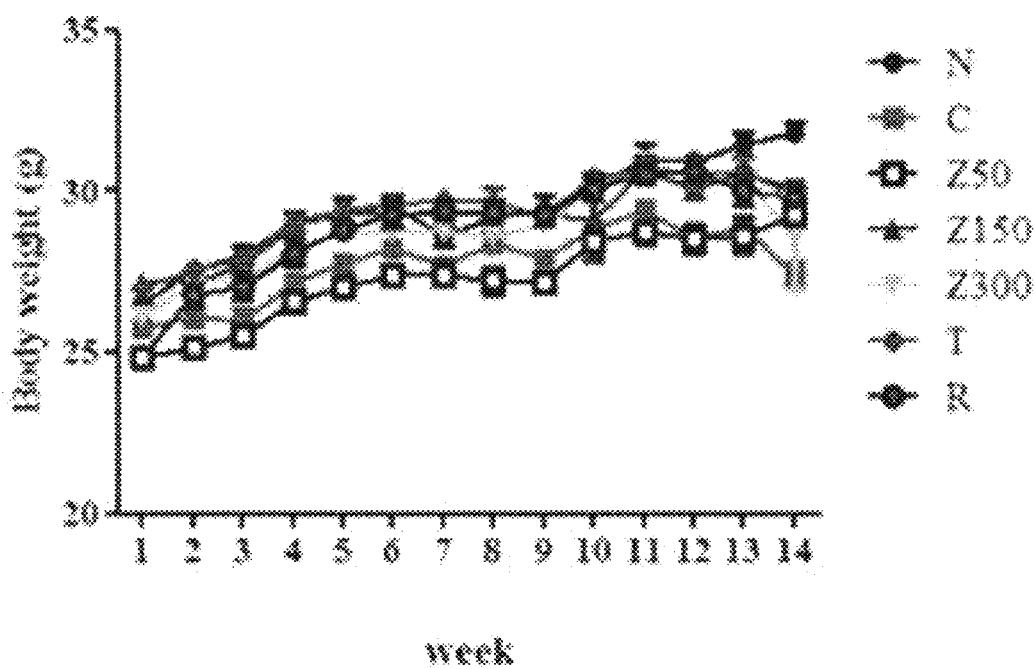
[FIG. 16]
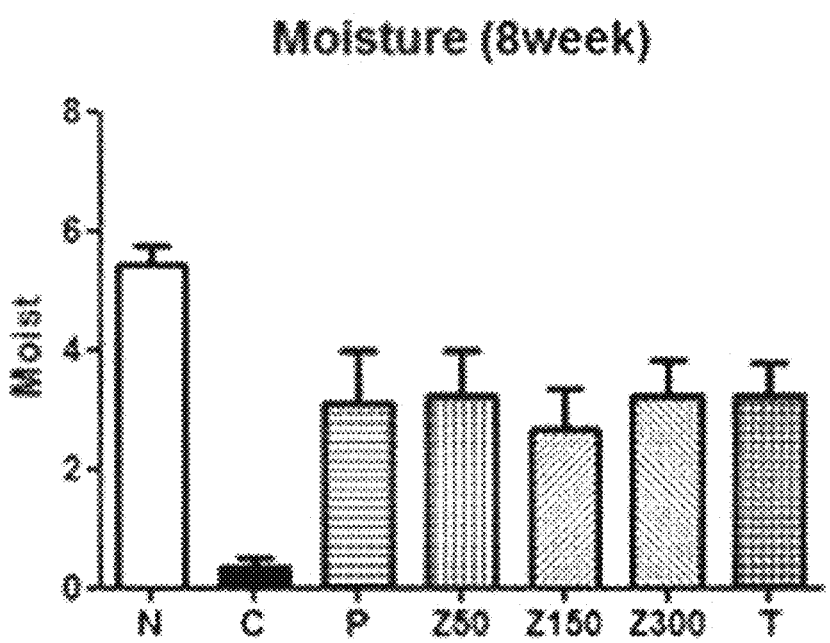

[FIG. 17]
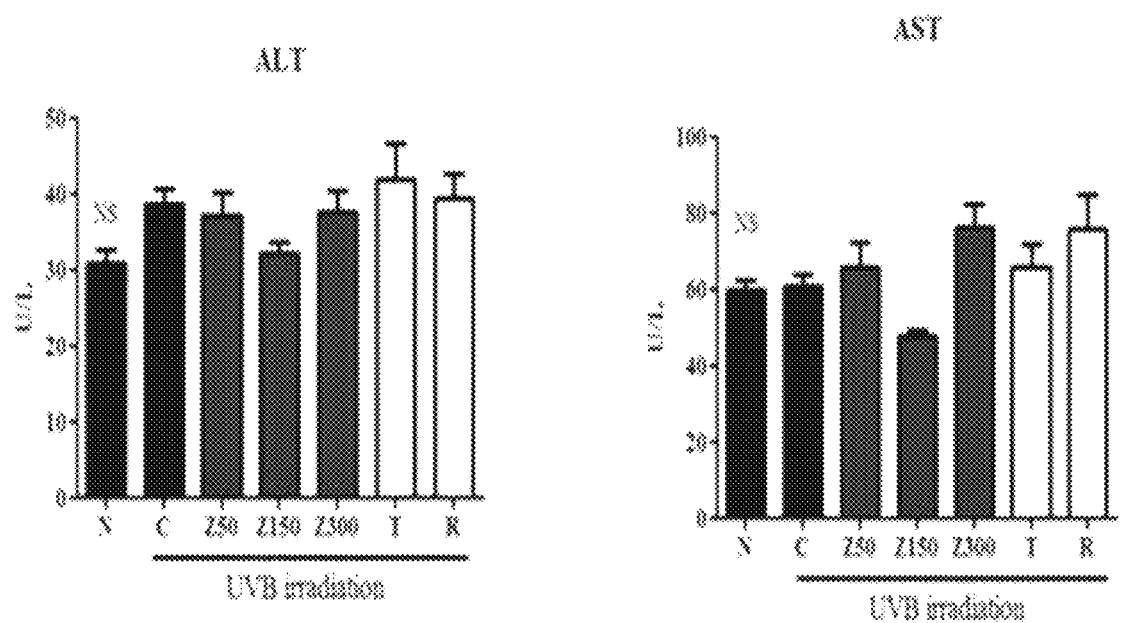

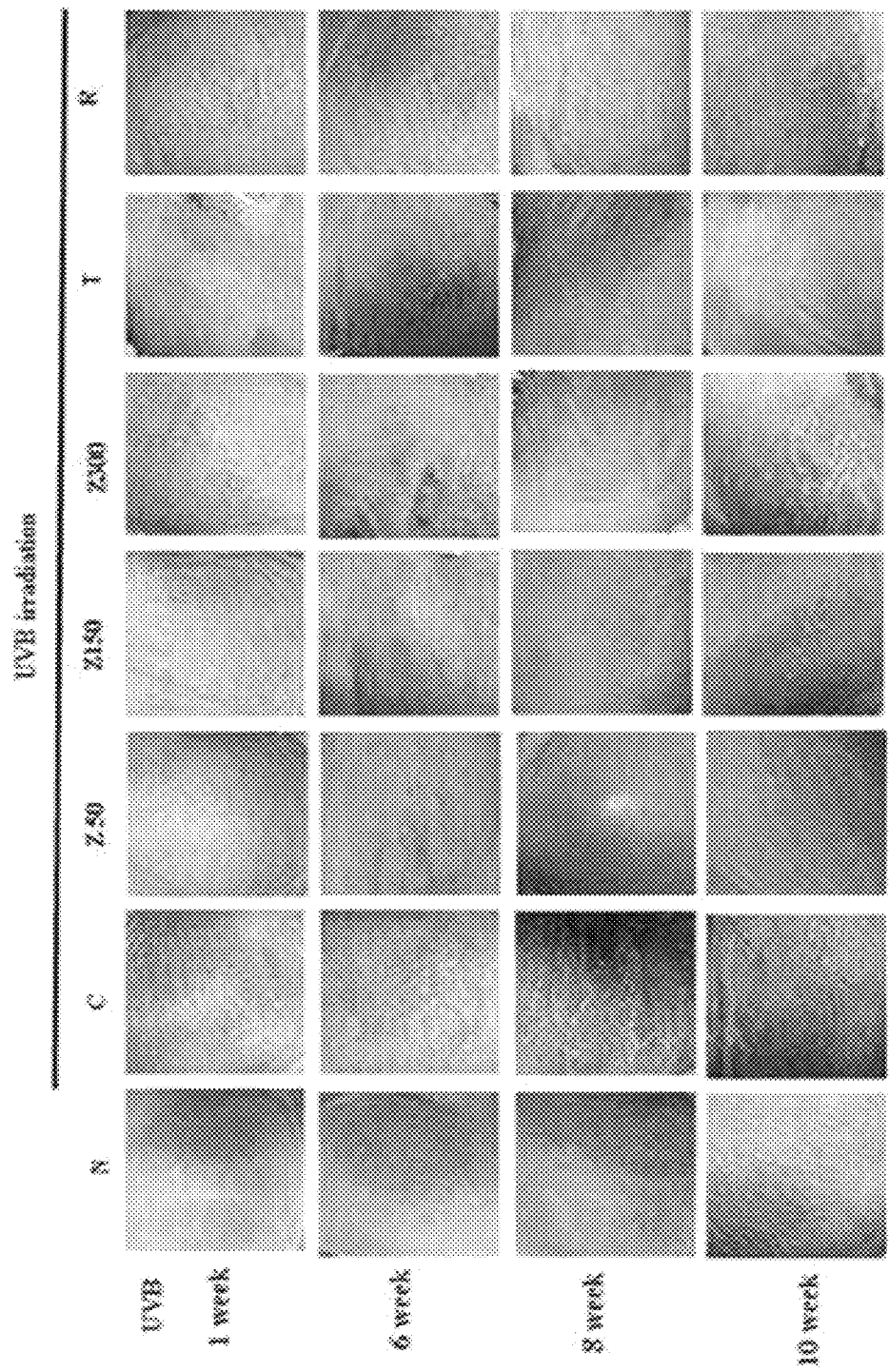
[FIG. 18]

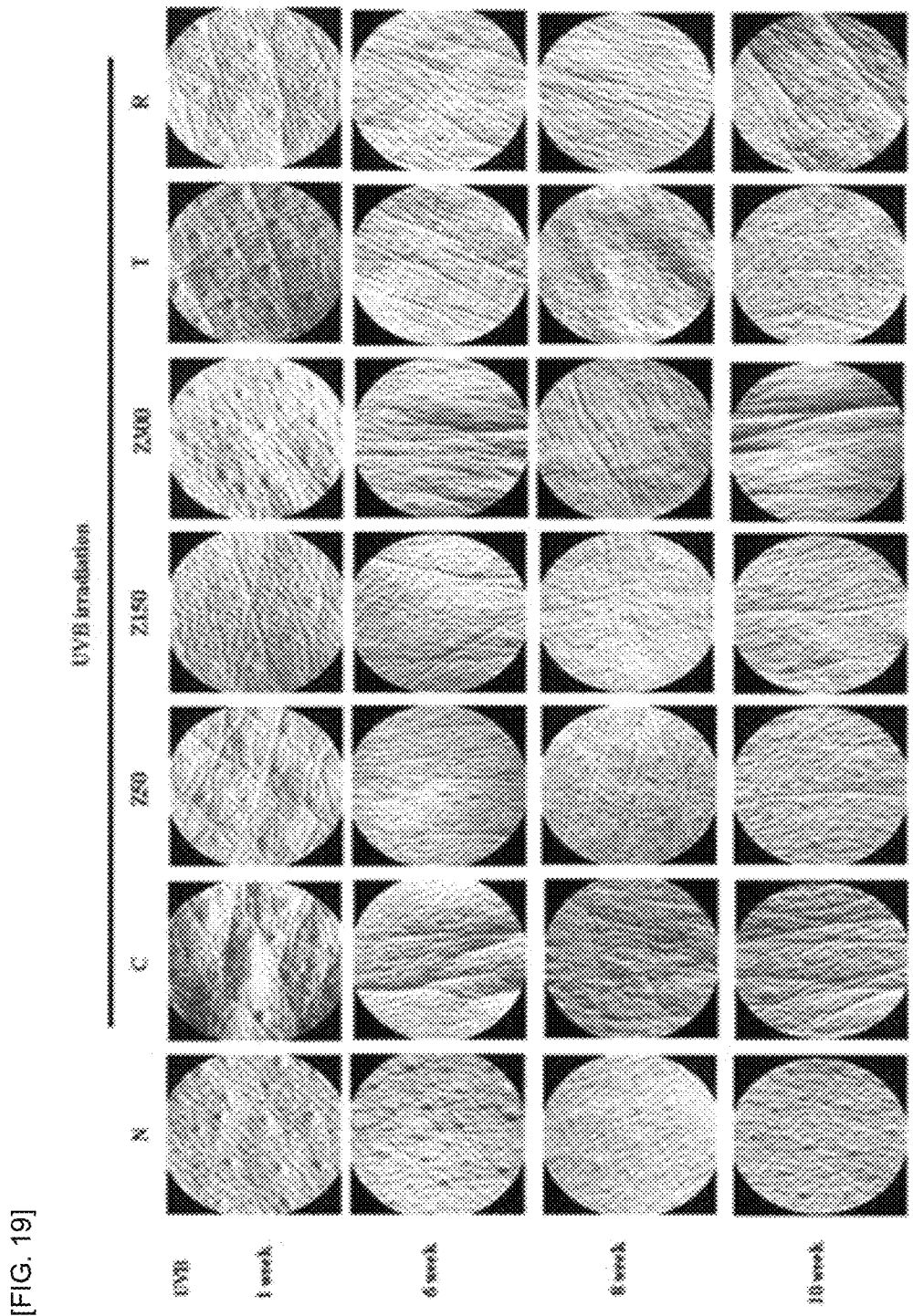
[FIG. 19]

[FIG. 20]
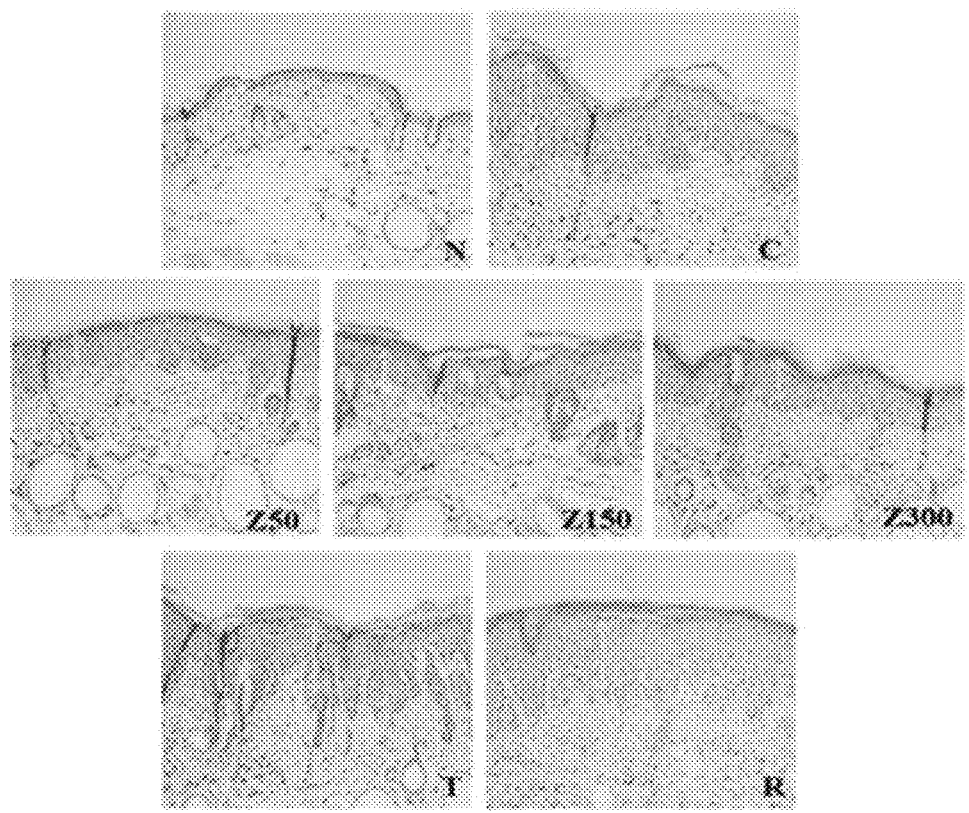

[FIG. 21]
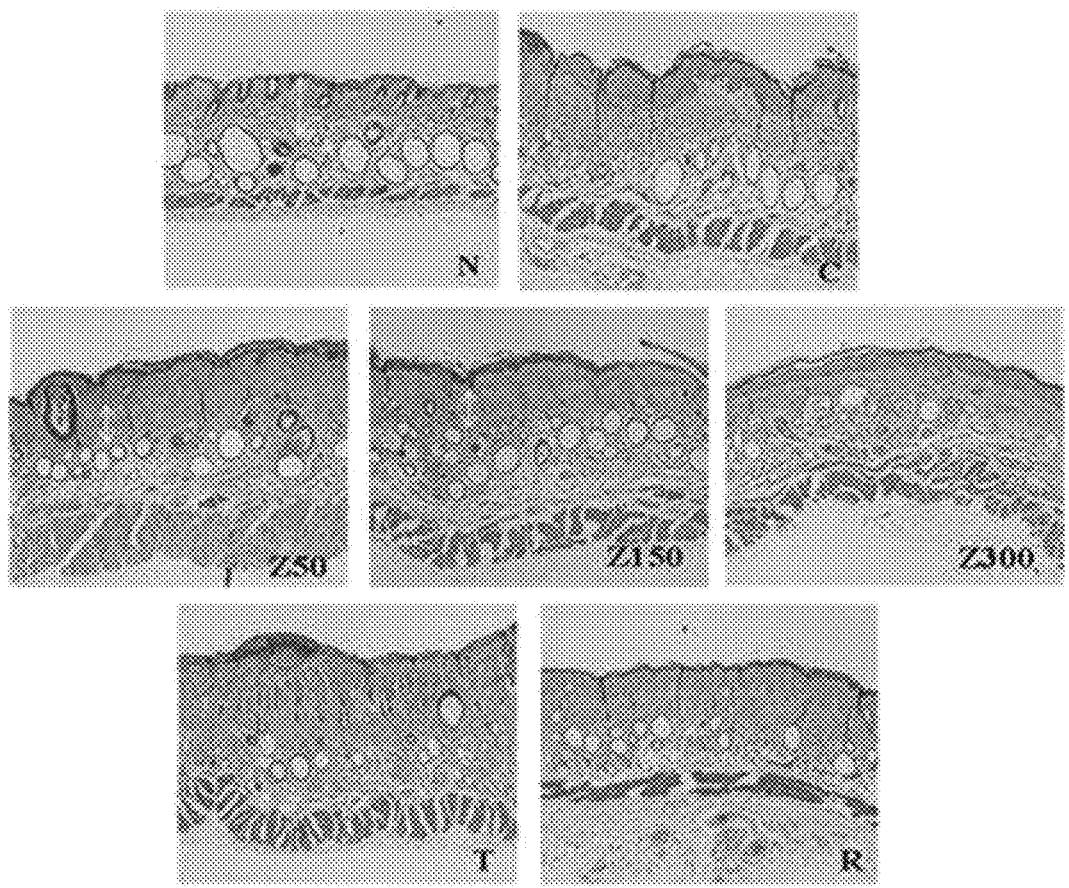

[FIG. 22]
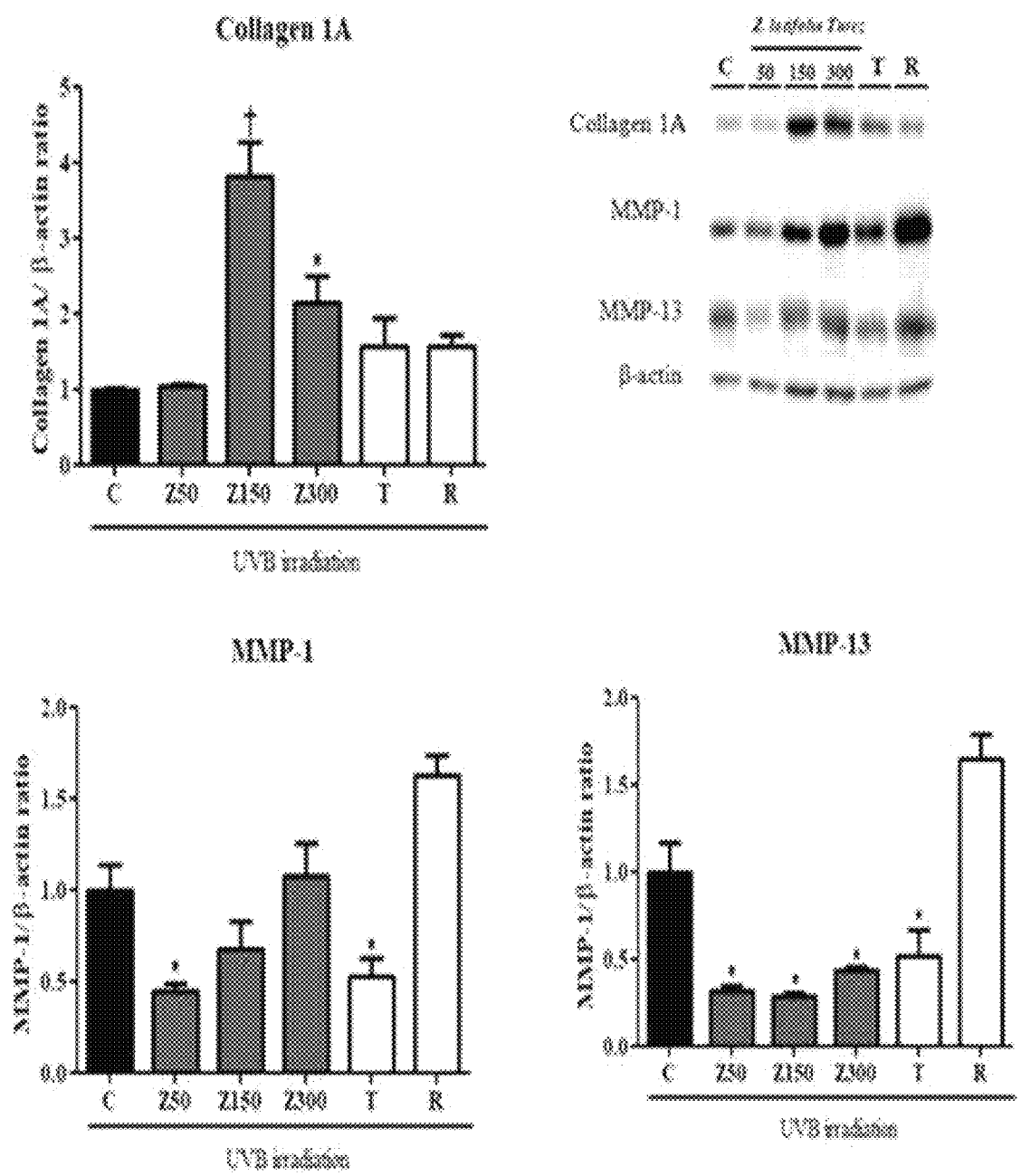

[FIG. 23]
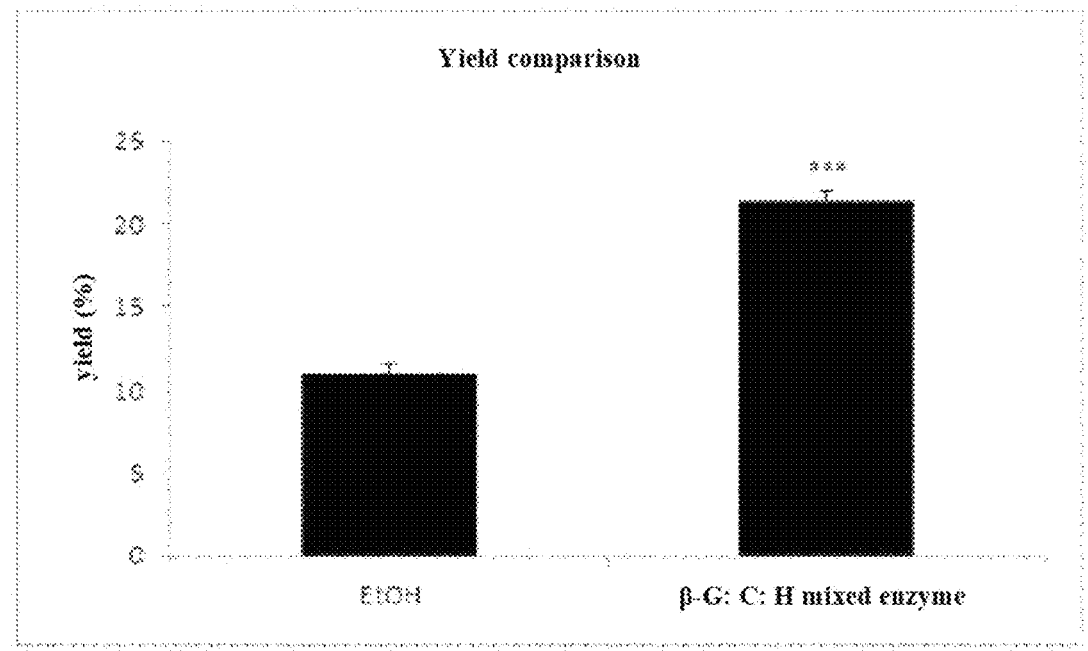
[FIG. 24]
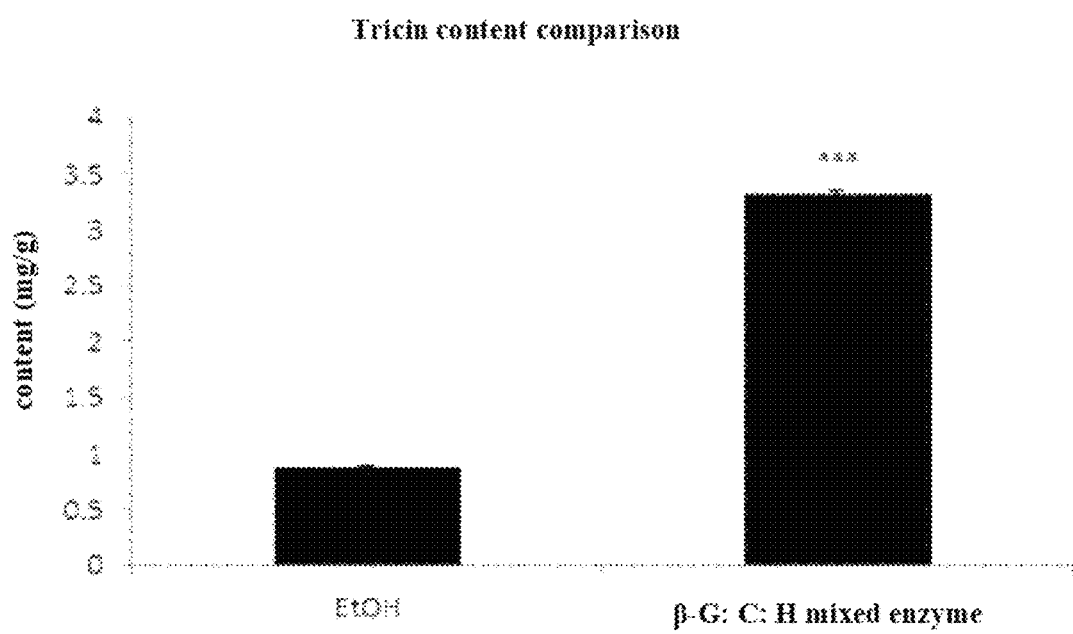

[FIG. 25]
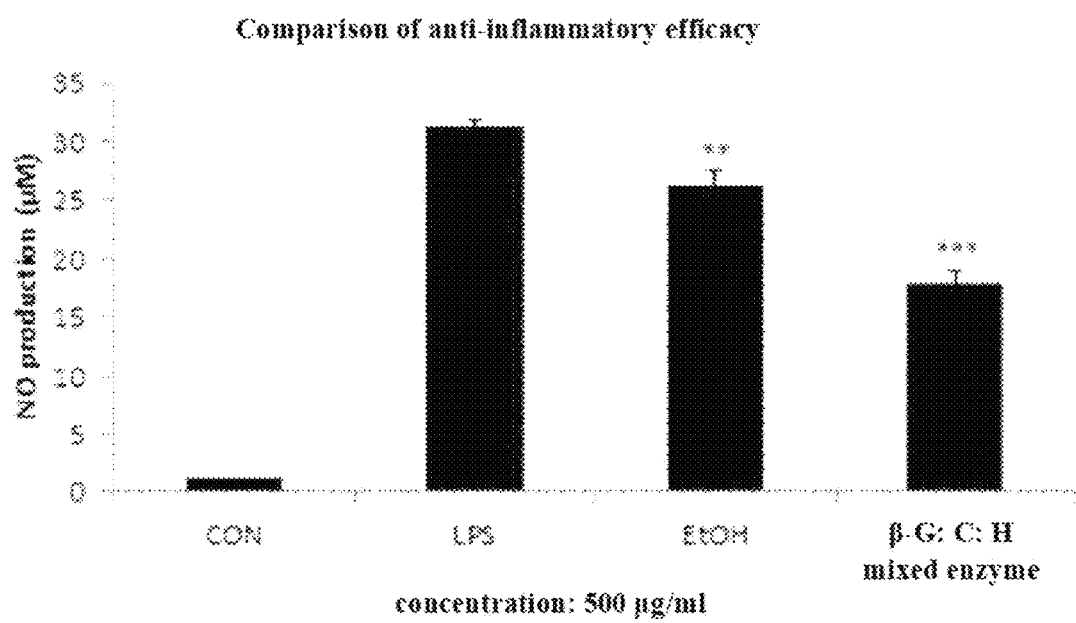
[FIG. 26]
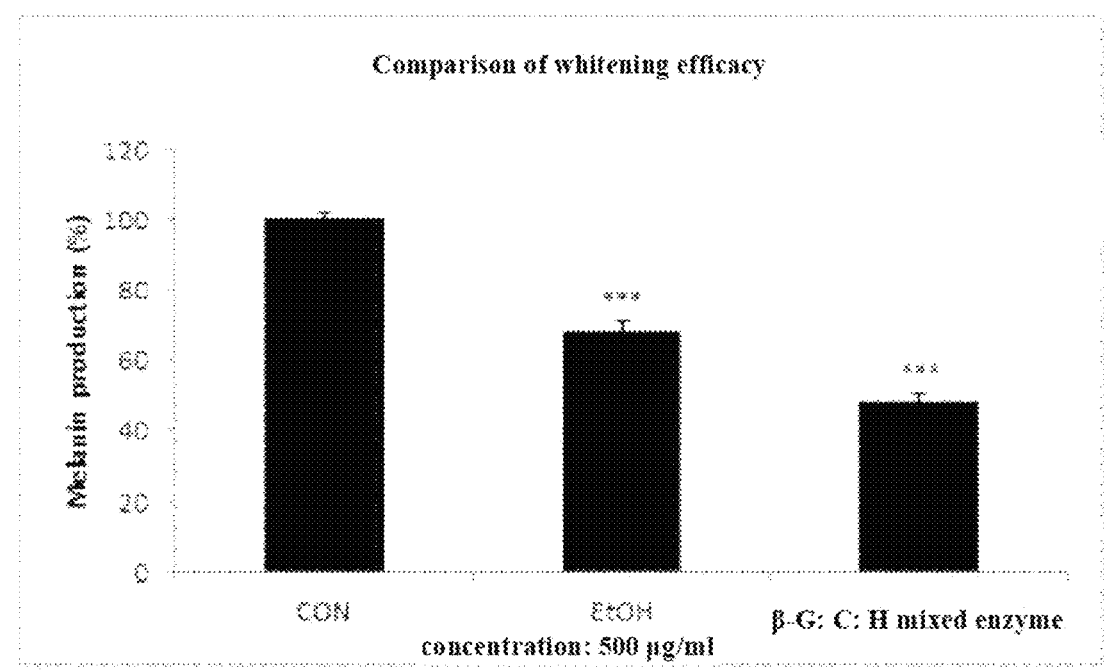

[FIG. 27]
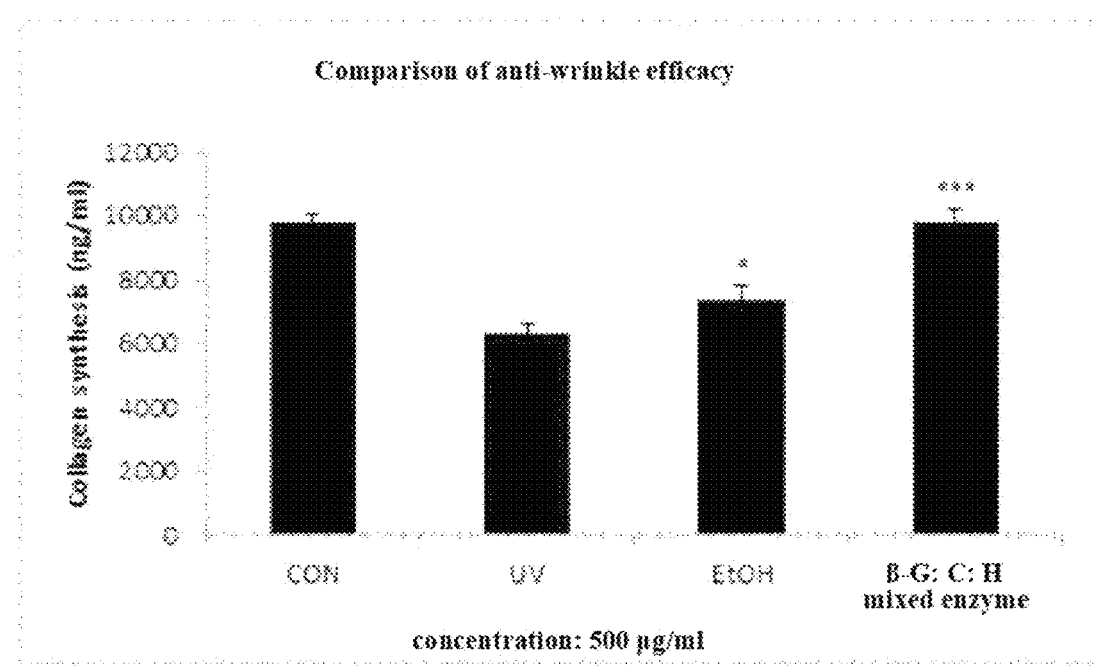
[FIG. 28]
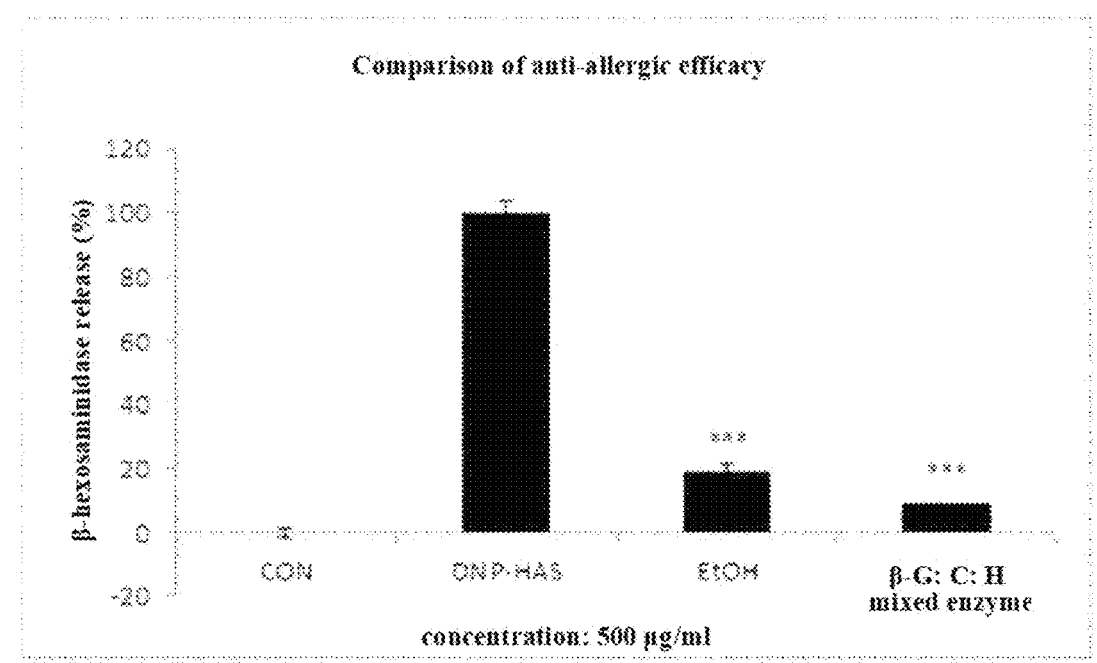

METHOD FOR PREPARING ENZYME-TREATED ZIZANIA LATIFOLIA TURCZ. EXTRACT HAVING INCREASED TRICIN CONTENT, AND COMPOSITION FOR WHITENING, WRINKLE REDUCTION, ANTI-INFLAMMATION, ANTI-ALLERGY AND MOISTURIZATION, PREPARED THEREBY

CROSS REFERENCE TO PRIOR APPLICATIONS

This application is the 35 U.S.C. 371 national stage of International application PCT/KR2019/011352 filed on Sep. 3, 2019; which claims priority to Korean application 10-2018-0160061 filed on Dec. 12, 2018. The entire contents of each of the above-identified applications are hereby incorporated by reference.

TECHNICAL FIELD

The present invention relates to a method of preparing an enzyme-treated extract of Zizania *latifolia* Turcz. with increased tricin content, and to a cosmetic composition or health functional food composition for whitening, wrinkle improvement, anti-inflammation, anti-allergy and moisturizing prepared thereby.

BACKGROUND ART

Zizania *latifolia* Turcz. is a perennial grass belonging to the Gramineae family and is called Zizania. It is known to be effective against diseases such as hypertension, paralysis, constipation, obesity and arteriosclerosis, and among the people, it is effective to drink the decoction of Zizania *latifolia* Turcz. or drink the juice thereof to a person who is suffering from pesticide poisoning, chemical poisoning, food poisoning, etc. In addition, recently, healthy foods and liquid tea using Zizania *latifolia* Turcz. have been developed (Korean Patent Publication No. 10-2010-0104334, Korean Patent Publication No. 10-2009-0127970).

The active substances contained in Zizania *latifolia* Turcz. are glycosides of tricin and derivatives thereof are bound by highly hydrophilic sugar molecules, which may result in low intestinal cell membrane lipid permeability and low absorption in the body. However, since the carbon skeleton itself, except for the sugar molecule, has high hydrophobicity, its solubility in the intestinal membrane lipid is high and thus it is easy to permeate the intestinal cell membrane. Therefore, high activity can be expected by increasing the absorption rate in the body by converting the glycosides of tricin and derivatives thereof, which may lower the intestinal absorption rate, to tricin.

Also, a document discloses that in the case of various flavonoid glycosides, the desired activity is further increased by converting to a non-glycoside, and thus the functions of whitening, wrinkle improvement, anti-inflammatory, anti-allergy and moisturizing can be increased by converting a glycoside to a non-glycoside.

However, in the method of extracting an active ingredient exhibiting efficacy, simple extraction such as normal temperature extraction or shaking extraction using an extraction solvent such as methanol or ethanol may result in less efficacy of the active ingredient because of low content of the non-glycoside active ingredient with high bioavailability.

On the other hand, in the manufacturing process of health functional foods, the sugar decomposition process of the glycosides of substance is mostly carried out through high temperature treatment with acid or fermentation and enzyme treatment. However, the fermentation process has a disadvantage in that it is difficult to meet the standard because the state of the microorganism, the growth condition, etc. must be kept constant, and the variation of the active ingredient content of the extract may increase due to the change of the enzyme secreted according to the state of the microorganism. In addition, the treatment process with acid at high temperature has the advantage of converting the glycoside material to the non-glycoside relatively easily, but it is difficult to secure the stability and reproducibility of the material in terms of chemistry under harsh conditions.

On the other hand, the enzyme treatment process is relatively simple in terms of material stability and process compared to the previously suggested process, so it has good advantages for commercialization. When the enzyme treatment process is established using enzymes secreted by microorganisms, it is thought that it will help to stably induce non-glycoside active ingredients by reducing the content variation of the active ingredient in the final extract to secure the stability of the material.

The present inventors sought a method of effectively converting tricin glycoside present in Zizania *latifolia* Turcz. to non-glycosylated forms with increased efficacy in whitening, wrinkle improvement, anti-inflammatory, anti-allergy and moisturizing, and increased bioavailability, and as a result, confirmed that the enzymatic reaction using a specific mixture of various enzymes is more effective in converting the tricin glycoside to the non-glycoside form than simply converting the non-glycoside by a single enzyme, and thus completed the present invention.

DISCLOSURE

Technical Problem

An object of the present invention is to provide a method of preparing an enzyme-treated Zizania *latifolia* Turcz. extract capable of maximizing the content of tricin.

Other object of the present invention is to provide a cosmetic composition having an enhanced various functionality from maximized tricin content.

Another object of the present invention is to provide a health functional food composition having an enhanced various functionality from maximized tricin content.

Technical Solution

In order to achieve the above object, the present invention provides a method of preparing an enzyme-treated Zizania *latifolia* Turcz. extract comprising: (1) adding water to Zizania *latifolia* Turcz. and hot water dipping; (2) cooling dipped product after hot water dipping in step (1) and treating with one or more enzyme selected from the group consisting of α-amylase, β-galactosidase, xylanase, lactase, lipase, tannase, cellulase, hemicellulase, pectinase and β-glucosidase to react and then filtering to obtain an enzyme-treated extract; (3) extracting the remaining residue after filtering in step (2) with any one solvent selected from the group consisting of water, lower alcohols of C1 to C4 and mixtures thereof to obtain a secondary extract; and (4) mixing the enzyme-treated extract of step (2) and the secondary extract of step (3) and concentrating or drying it.

In order to achieve the above other object, the present invention provides a cosmetic composition comprising the enzyme-treated Zizania *latifolia* Turcz. extract prepared by the preparation method as an active ingredient, wherein the enzyme-treated Zizania *latifolia* Turcz. extract contains 0.01% to 90% by weight of tricin.

In order to achieve the above another object, the present invention provides a health functional food composition comprising the enzyme-treated Zizania *latifolia* Turcz. extract prepared by the preparation method as an active ingredient, wherein the enzyme-treated Zizania *latifolia* Turcz. extract contains 0.01% to 90% by weight of tricin.

Advantageous Effects

The present invention relates to a method of preparing an enzyme-treated Zizania *latifolia* Turcz. extract and a composition comprising the enzyme-treated Zizania *latifolia* Turcz. extract, and the method according to the present invention includes mixing or complex processing steps of various enzymes, and the enzyme-treated Zizania *latifolia* Turcz. extract has maximized yield and the content of tricin to be usefully utilized as an cosmetic composition or health functional food composition having high bioavailability and increased activities in skin whitening, moisturizing, anti-inflammatory, anti-allergy and anti-wrinkle.

DESCRIPTION OF DRAWINGS

FIG. 1 shows a process diagram schematically showing a method of preparing an enzyme-treated Zizania *latifolia* Turcz. extract according to an embodiment of the present invention.

FIG. 2 is a graph showing the yield of ethanol-treated and enzyme-treated extracts of Zizania *latifolia* Turcz. according to the present invention (* $p<0.05$ versus EtOH,  $p<0.01$ versus EtOH, * $p<0.001$ versus EtOH).

FIG. 3 is a graph showing the analysis results of tricin content of ethanol-treated and enzyme-treated extracts of Zizania *latifolia* Turcz. according to the present invention (* $p<0.05$ versus EtOH,  $p<0.01$ versus EtOH, * $p<0.001$ versus EtOH).

FIG. 4 shows a tricin analysis chromatogram of ethanol-treated and enzyme-treated extracts of Zizania *latifolia* Turcz.

FIG. 5 is a graph showing the total amount of tricin considering the yield of ethanol-treated and enzyme-treated extracts of Zizania *latifolia* Turcz. (* $p<0.05$ versus EtOH,  $p<0.01$ versus EtOH, * $p<0.001$ versus EtOH).

FIG. 6 shows a result confirming the anti-inflammatory efficacy of ethanol-treated and enzyme-treated extracts of Zizania *latifolia* Turcz. (# $p<0.01$ versus LPS, * $p<0.05$ versus EtOH, ** $p<0.01$ versus EtOH).

FIG. 7 shows a result confirming the anti-inflammatory efficacy according to the concentration of tricin (* $p<0.05$ versus LPS,  $p<0.01$ versus LPS, * $p<0.001$ versus LPS).

FIG. 8 shows a result confirming the whitening efficacy of ethanol-treated and enzyme-treated extracts of Zizania *latifolia* Turcz. (# $p<0.01$ versus CON, * $p<0.05$ versus EtOH,  $p<0.01$ versus EtOH, * $p<0.001$ versus EtOH).

FIG. 9 show a result confirming the whitening efficacy according to the concentration of tricin (* $p<0.05$ versus CON,  $p<0.01$ versus CON, * $p<0.001$ versus CON).

FIG. 10 shows a result confirming the wrinkle improvement efficacy of ethanol-treated and enzyme-treated extracts of Zizania *latifolia* Turcz. (# $p<0.05$ versus UV, * $p<0.05$ versus EtOH, ** $p<0.01$ versus EtOH).

FIG. 11 is a result confirming the wrinkle improvement efficacy according to the concentration of tricin (* $p<0.05$ versus CON,  $p<0.01$ versus CON, * $p<0.001$ versus CON).

FIG. 12 shows a result confirming the anti-allergic efficacy of ethanol-treated and enzyme-treated extracts of Zizania *latifolia* Turcz. (# $p<0.001$ versus DNP-HAS, * $p<0.05$ versus EtOH).

FIG. 13 shows a result confirming the anti-allergic efficacy according to the concentration of tricin (*** $p<0.001$ versus DNP-HSA).

FIG. 14 shows the design of an animal experiment.

FIG. 15 is a graph showing the change in weight of the experimental group in the animal experiment.

FIG. 16 is a graph showing the moisture level on skin surface of the experimental group in the animal experiment.

FIG. 17 is a graph showing the results of the serum test of the experimental group in the animal experiment.

FIG. 18 shows a result of visual observation of the back surface of the experimental group in the animal experiment.

FIG. 19 is a photograph of observing by the SILFLO microscope of the experimental group in the animal experiment.

FIG. 20 is a photograph showing results of H&E staining of the experimental group in the animal experiment.

FIG. 21 is a photograph showing results of Masson's Trichrome staining of the experimental group in the animal experiment.

FIG. 22 shows a result of confirming protein expression of skin tissue when irradiated with UVB to the experimental group in the animal experiment.

FIG. 23 shows a graph of comparing the yields of ethanol extract and enzyme-treated extract of Zizania *latifolia* Turcz. under established extraction conditions.

FIG. 24 shows a graph comparing the tricin content of ethanol extract and enzyme-treated extract of Zizania *latifolia* Turcz. under established extraction conditions.

FIG. 25 shows a graph comparing the anti-inflammatory efficacy of ethanol extract and enzyme-treated extract of Zizania *latifolia* Turcz. under established extraction conditions ( $p<0.01$ versus LPS, * $p<0.001$ versus LPS).

FIG. 26 shows a graph comparing the whitening efficacy of ethanol extract and enzyme-treated extract of Zizania *latifolia* Turcz. under established extraction conditions (*** $p<0.001$ versus CON).

FIG. 27 shows a graph comparing the wrinkle improvement efficacy of ethanol extract and enzyme-treated extract of Zizania *latifolia* Turcz. under established extraction conditions (* $p<0.05$ versus UV, *** $p<0.001$ versus UV).

FIG. 28 shows a graph comparing the anti-allergic efficacy of ethanol extract and enzyme-treated extract of Zizania *latifolia* Turcz. under established extraction conditions (*** $p<0.001$ versus DNP-HAS).

BEST MODE

The active substances contained in the Zizania *latifolia* Turcz. extract are the glycosides of tricin or derivatives thereof and these are bound by highly hydrophilic sugar molecules, so the solubility in intestinal cell membrane lipid is low and the absorption rate in the body is likely to be low. To overcome this problem, the inventors of the present invention has studied a method of increasing the bioavailability by decomposing the sugars of glycosides of tricin and derivatives thereof and by increasing efficacies of anti-inflammatory, skin whitening, wrinkle improvement, anti-allergy and moisturizing by converting to non-glycosides with superior activity than glycosides of tricin and derivatives thereof.

Accordingly, in one example of the present invention, the extract of the Zizania latifolia Turcz. extracted by the preparation method disclosed in the present invention has an increased tricin content, thereby increasing anti-inflammatory, skin whitening, anti-allergy, wrinkle improvement and moisturizing efficacy. In addition, the yield was also increased by about 2 times from 11% to 20.8%, and commercial mass production was possible, thus an enzyme-treated extract of Zizania latifolia Turcz. with high value for a cosmetic raw material and functional food. It is presumed that the reason why various efficacy is increased is because precursors of the tricin glycoside and derivatives thereof contained in the extract of Zizania latifolia Turcz., such as tricin-7-O-β-D-glucopyranose and tricin derivatives such as tricin-4'-O-(threo-β-guaiacylglyceryl) ether 7-o-β-D-glucopyranose, tricin-4'-O-(erythro-β-guaiacylglyceryl) ether 7-o-β-D-glucopyranose, tricin-4'-O-(threo-β-guaiacylglyceryl) ether 7"-O-β-D-glucopyranose, tricin-4'-O-(erythro-β-guaiacylglyceryl) ether 7-o-β-D-glucopyranose, and Salcolin A, Salcolin B, Salcolin C, and Salcolin D, have been converted to tricin, which shows high activity through enzymatic reaction. The method of preparing the enzyme-treated extract of Zizania latifolia Turcz. according to the present invention is schematically illustrated in FIG. 1.

Thus, the present invention provides a method of preparing an enzyme-treated Zizania latifolia Turcz. extract comprising: (1) adding water to Zizania latifolia Turcz. and hot water dipping; (2) cooling dipped product after hot water dipping in step (1) and treating with one or more enzyme selected from the group consisting of α-amylase) [EC 3.2.1.1], β-galactosidase [EC 3.2.1.23], xylanase [EC 3.2.1.8], lactase [EC 3.2.1.108], lipase [EC 3.1.1.3], tanase [EC 3.1.1.20], cellulase [EC 3.2.1.4], hemicellulase [EC 232-799-9], pectinase [EC 3.2.1.15] and β-glucosidase [EC 3.2.1.21] to react and then filtering to obtain an enzyme-treated extract; (3) extracting the remaining residue after filtering in step (2) with any one solvent selected from the group consisting of water, lower alcohols of C1 to C4 and mixtures thereof to obtain a secondary extract; and (4) mixing the enzyme-treated extract of step (2) and the secondary extract of step (3) and concentrating or drying it.

Preferably, in the step (1), the hot water dipping may be performed by adding 1 to 100 parts by weight of water with respect to 1 part by weight of the Zizania latifolia Turcz. at 20° C. to 130° C. for 5 minutes to 100 hours, more preferably, by adding 1 to 50 parts by weight of water with respect to 1 part by weight of the Zizania latifolia Turcz. at 50° C. to 120° C. for 30 minutes to 100 hours, most preferably, by adding 5 to 30 parts by weight of water to the Zizania latifolia Turcz. at 70° C. to 120° C. for 30 minutes to 4 hours.

In the step (2), cooling may be performed at 10° C. to 90° C., and preferably at 20° C. to 45° C.

In addition, in the step (2), it may be treated with the enzyme in amount of 0.1 to 80 parts by weight with respect to 100 parts by weight of the dipped product immersion. If the amount of the enzyme is too small outside the numerical range, it is difficult to smoothly separate and convert tricin present in the hot water immersion of Zizania latifolia Turcz. from the precursor and conversely, if too much is treated, substances other than the tricin precursor which are not involved in the activity are extracted together in a high content and an extract having a relatively low content of tricin and a reduced efficacy may be prepared, and it is not preferable because it may affect the cost of the manufacturing process commercially.

At this time, in the step (2), the enzyme may be treated and reacted at 10° C. to 90° C. for 5 minutes to 120 hours, preferably at 20° C. to 80° C. for 5 minutes to 120 hours, more preferably at 30° C. to 60° C. for 5 minutes to 48 hours, most preferably at 20° C. to 45° C. for 8 hours to 24 hours, and the appropriate reaction time of the enzyme is inversely proportional to the amount of the enzyme added and thus the more the amount of enzyme added, the shorter the reaction time.

However, when the reaction time after the enzyme treatment is less than the numerical range, the time for the enzyme treatment is too short, so the conversion rate from the tricin precursor present in the hot water immersion of Zizania latifolia Turcz. to tricin is lowered, and conversely, the enzyme treatment reaction time exceeds the numerical range, it is not preferable because it may affect the manufacturing process cost commercially.

In order to achieve the object of the present invention, the complex of the enzymes may be used in combination of one or more complex enzymes of purified single enzymes or commercialized complex enzyme. As an example of a commercialized enzyme, it may be at least one selected from commercial enzymes plantase TL, rapidase C80 MAX, biscozyme L, smizyme SPC, smizyme AC, pectinex Ultra SP-L, pectinex Ultra pulp, and viscoflow MG, but it is not limited thereto.

In one example of the present invention, in the step (2), three enzymes of β-glucosidase, cellulase and hemicellulase may be simultaneously treated and particularly, when three kinds of enzymes are mixed and the content and yield of various tricins are the highest and the functionality is also excellent, which is preferable.

In one example of the present invention, in the step (2), the enzyme may convert a flavonoid glycoside contained in the Zizania latifolia Turcz. to a flavonoid non-glycoside.

Glycosides of tricin and derivatives are glycosides in which the binding of sugars is R—O-β-D-glucopyranose, and glucose is bound to the structure of tricin and derivatives by beta binding. The most representative enzyme that decomposes glucose bound with beta binding is beta-glucosidase enzyme. To utilize this, an enzyme reaction was conducted with reference to the present invention, but as a result, an increase in tricin content was hardly observed, and no significant changes were observed in the efficacy of whitening, wrinkle improvement, inflammation improvement, allergy improvement and moisturizing. Beta-glucosidase enzyme, which is known as an enzyme that breaks down beta bonds, is generally known to be involved in the breakdown of sugar molecules bound to anthocyanins in the final ripening stage of fruits. It is thought that anthocyanin is a family of anthocyanidins and has a distinct difference in molecular structure and the position to which the sugar is attached from tricin of a family of flavone, as shown in Chemical Formula 1 below, and thus the reaction does not occur as shown in Chemical Formula 2 due to the substrate specificity.

[Chemical Formula 1]

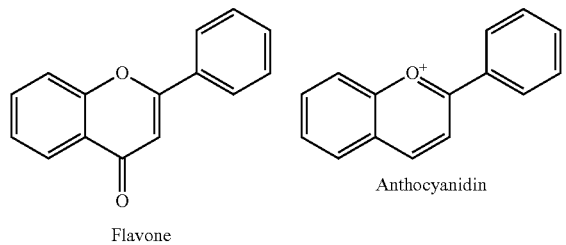

Flavone          Anthocyanidin

[Chemical Formula 2]

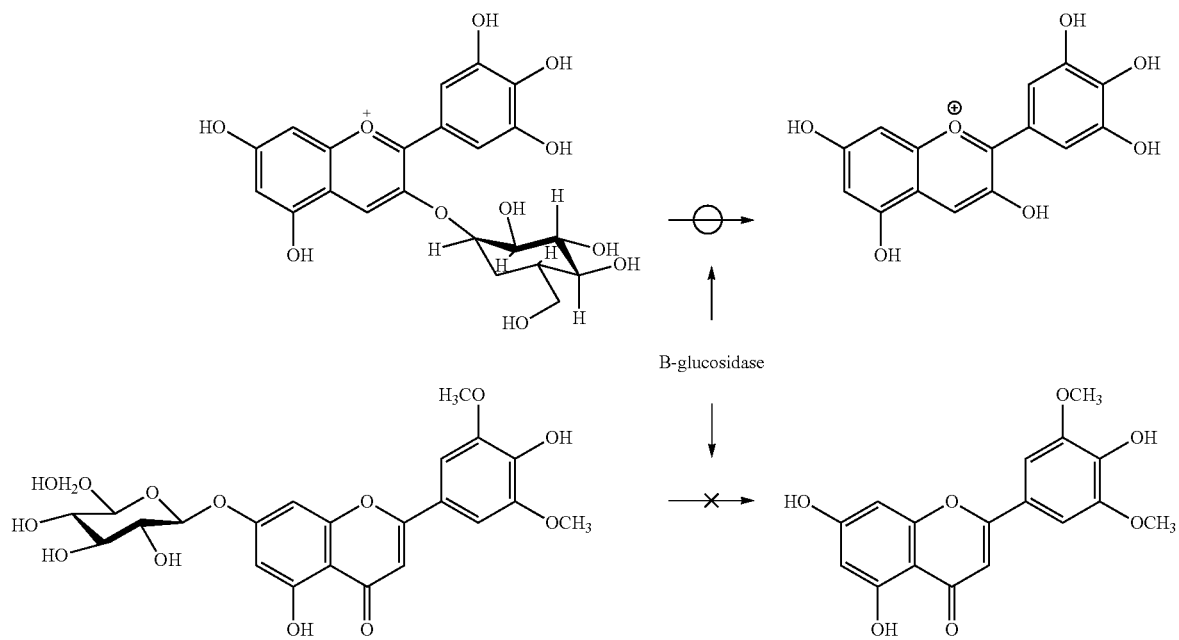

The structure of tricin is structurally inconsistent with the active site of the beta-glucosidase enzyme, just as, even if it contains a similar structure as described above, the activity of the enzyme to be treated varies due to the specificity of the substrate, and it is thought that the glycolysis of tricin glycosides did not proceed smoothly.

In the step (3), the residue may be extracted with 1 to 100 parts by weight of water or alcohol aqueous solution as a solvent with respect to 1 part by weight of the residue at 20° C. to 130° C. for 10 minutes to 100 hours, preferably at 20° C. to 100° C. for 2 to 12 hours, or the residue may be extracted with 1 to 30 parts by weight of water or alcohol aqueous solution as a solvent with respect to 1 part by weight of the residue at 50° C. to 100° C. for 30 minutes to 10 hours. If the extraction temperature is less than the above range, the extraction yield of tricin and active ingredients in activity is lowered. If the extraction temperature exceeds the above range, the active ingredients are destroyed, or substances not involved in the activity are extracted together in a high content, and thus an extract with reduced efficacy can be obtained, which is not preferable.

In one embodiment of the present invention, the alcohol may be an aqueous ethanol solution of 5 to 95% by weight, preferably an aqueous ethanol solution of 20 to 80% by weight, more preferably an aqueous ethanol solution of 50 to 70% by weight, most preferably an aqueous ethanol solution of 70% by weight.

That is, most preferably, in the step (3), the extraction may be carried out for 6 hours at 80° C. using 70% ethanol as a solvent, and when extracted under these extraction conditions, the content of tricin, yield and functionality are maximized and thus is preferable.

In addition, the mixture may be concentrated to obtain a concentrate, or the concentrate may be dried to obtain an extract in powder form.

According to an example of the present invention, a pretreatment step of irradiating ultrasonic waves or microwaves may be further performed before extraction of the step (3), and the irradiation of ultrasonic waves and microwaves may be used in combination. In the case of irradiating ultrasonic or/and microwaves to the enzyme-treated extract of Zizania latifolia Turcz., it is preferable to obtain an extract with improved inflammation, skin whitening, wrinkle improvement, allergy improvement, and moisturizing functionalities as compared to the case of not being irradiated.

The ultrasonic waves may be irradiated at 15 to 25 kHz and 500 to 800 watts for 2 to 30 minutes, and the microwave may be irradiated at 2000 to 3000 MHz and 50 to 400 watts for 5 to 60 seconds. If the irradiation energy and time are less than the above range, the effect by irradiation is negligible, and if they exceed the above range, the extraction rate of substances not involved in activity increases, which is not preferable.

On the other hand, for the enzyme-treated extract of Zizania *latifolia* Turcz., it can remove impurities using a conventional filtration method or device, for example, by using a centrifugal separation method or a filter media or a micro filter to obtain extract with removed impurities. The filter media may be 1 to 200 μm, and the micro filter may be a 0.2 to 0.8 μm filter, but it is not limited thereto.

The above enzyme-treated extract of Zizania *latifolia* Turcz. may be prepared in powder form after additional processes such as distillation under reduced pressure, lyophilization or spray drying, or may be prepared by a continuous process method by an enzyme immobilization method. According to the above method, it is possible to provide the enzyme-treated extract of Zizania *latifolia* Turcz. having a solids yield of 20% by weight or more.

The extract thus prepared can be filtered or concentrated or dried to remove the solvent, and filtering, concentrating and drying can be performed. For example, a filter paper or a vacuum filter may be used, and the concentration may be performed by using a reduced pressure concentrator, drying may include hot air drying, spray drying, low temperature drying, and freeze drying, but it is not limited to the specified method.

As described above, the enzyme-treated extract of Zizania *latifolia* Turcz. prepared by the above preparation method may contain 0.01% to 90% by weight of tricin, and thus can be used as a composition for whitening, wrinkle improvement, inflammation improvement, allergy improvement and moisturizing.

In the present invention, the tricin may be represented by the following Chemical Formula 3:

[Chemical Formula 3]

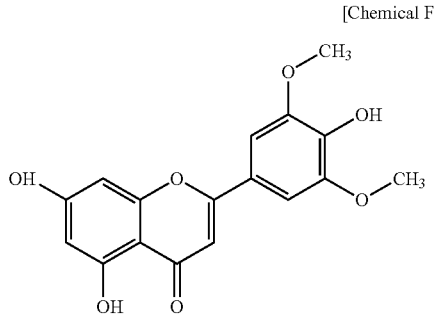

In addition, as the precursor of the tricin, the substances that affect the tricin content increase after enzyme treatment are as follows, and their chemical formulas are shown in the following Chemical Formula 4:

1. Tricin (1 in Chemical Formula 4)
2. Tricin-7-O-β-D-glucopyranose (2 in Chemical Formula 4)
3. Salcolin A (3 in Chemical Formula 4)
4. Salcolin B (4 of Chemical Formula 4)
5. Tricin-4'-O-(threo-β-guaiacylglyceryl) ether 7-O-β-D-glucopyranose (5 in Chemical Formula 4)
6. Tricin-4'-O-(erythro-β-guaiacylglyceryl) ether 7-O-β-D-glucopyranose (6 in Chemical Formula 4)
7. Tricin-4'-O-(threo-β-guaiacylglyceryl) ether 7-O-β-D-glucopyranose (7 in Chemical Formula 4)
8. Tricin-4'-O-(erythro-β-guaiacylglyceryl) ether 7-O-β-D-glucopyranose (8 in Chemical Formula 4)
9. Salcolin C (9 in Chemical Formula 4)
10. Salcolin D (Salcolin D) (10 in Chemical Formula 4)

[Chemical Formula 4]

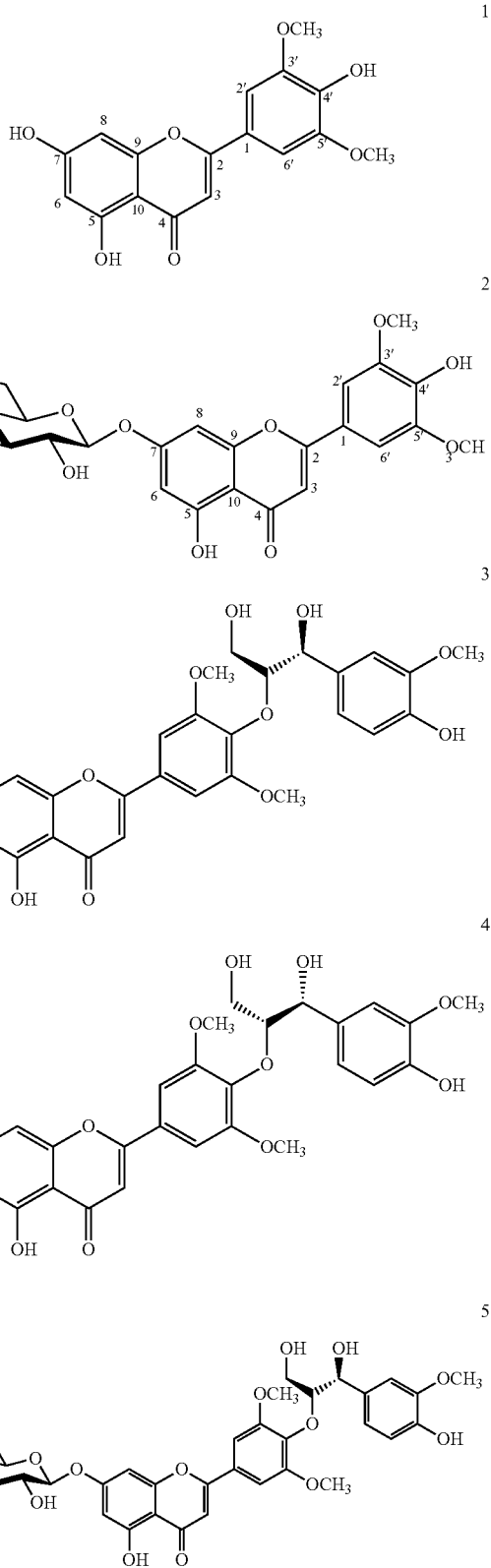

-continued

6

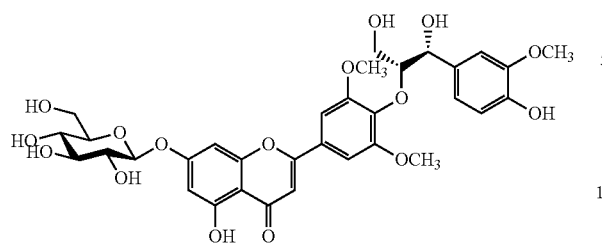

7

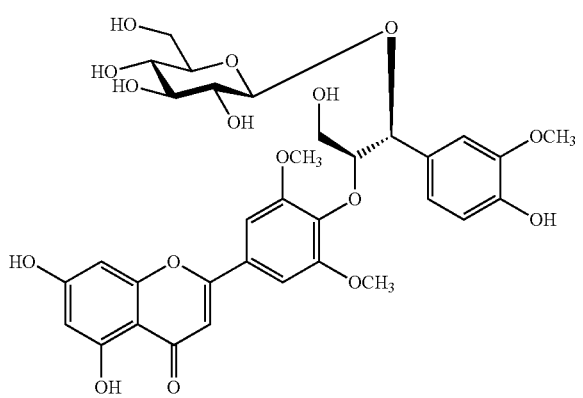

8

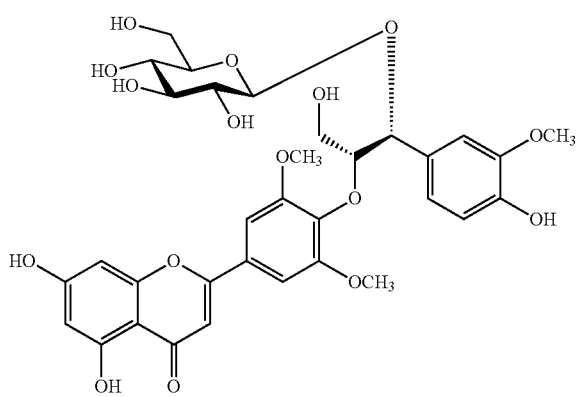

9

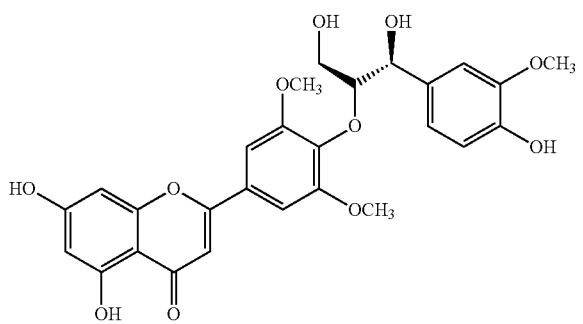

-continued

10

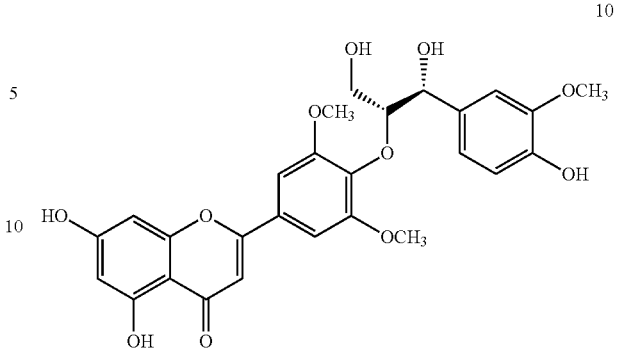

Therefore, the present invention provides a cosmetic composition comprising the enzyme-treated Zizania *latifolia* Turcz. extract prepared by the preparation method as an active ingredient, wherein the enzyme-treated Zizania *latifolia* Turcz. extract contains 0.01% to 90% by weight of tricin.

The cosmetic composition may be used for whitening, wrinkle improvement, inflammation improvement, allergy improvement or moisturizing, and contains a high content of tricin, thereby exhibiting excellent whitening, wrinkle improvement, inflammation improvement, allergy improvement and moisturizing effect.

In this specification, the term 'cosmetics' refers to substances that can be cosmetic or quasi-drugs. Cosmetics refer to products used in the human body to clean and beautify the human body to add attractiveness and to change the appearance brightly or to maintain or promote the health of the skin and hair, which have a slight effect on the human body. In addition, functional cosmetics are products that help to whiten the skin, help to improve the wrinkles of the skin, or help protect the skin from UV rays, including those prescribed by Ordinance of the Ministry of Health, Welfare and Family Affairs and collectively refer to anything that improves skin. Quasi-drug refers to drugs that meet the classification criteria set by the Ministry of Health and Welfare for items that have a slight effect on the human body rather than drugs used to treat or prevent disease. According to the Pharmaceutical Affairs Law, except for articles used for the purpose of medicines, textiles and rubber products used for the treatment or prevention of disease in humans and animals, non-mechanical or mechanical or similar articles which has a slight effect on the human body or does not act directly, and fungicides and pesticides to prevent infectious diseases. Typical examples of quasi-drugs include toothpaste, functional soap, functional shampoo and the like.

Namely, the cosmetic composition of the present invention can be used as quasi-drugs such as cosmetics for skin whitening, anti-aging, wrinkle improvement or skin elasticity enhancement (essence, cream, etc.), functional soap or skin cleansing foam, cleansing cream or cleansing water for whitening, anti-aging, wrinkle improvement or for skin elasticity enhancement.

In one example of the present invention, the Zizania *latifolia* Turcz. extract may be contained in an amount of 0.001 to 100% by weight based on the total weight of the composition, but it is not limited thereto.

The cosmetic composition may be combined with the above components as well as other components that are usually blended in cosmetic products as necessary. Other ingredients that may be added include fats and oils, moisturizers, emollients, surfactants, organic and inorganic pigments, organic powders, ultraviolet absorbers, preservatives, fungicides, antioxidants, plant extracts, pH adjusters, alcohols, pigments, fragrances, blood circulation accelerator, coolant, anhydrotics, purified water, sunscreen, and the like.

The components included in the cosmetic composition may further include components commonly used in cosmetic compositions in addition to the above compounds, for example, conventional adjuvants such as stabilizers, solubilizers, vitamins, pigments and fragrances, carriers, and moisturizers.

In addition, the cosmetic composition may be prepared in any formulation conventionally prepared in the industry, for example, it may be a formulation selected from emulsion, suspension, cream, tonic, essence, pack, gel, powder, lipstick, makeup base, foundation, lotion, ointment, patch, essence, cleansing foam, cleansing cream, cleansing water, body lotion, body cream, body oil, body essence, shampoo, rinse, body cleaner, soap and spray. The preparation method of these formulations may be prepared according to the preparation method of a conventional cosmetic formulation.

In addition, the present invention provides a health functional food composition comprising the enzyme-treated Zizania latifolia Turcz. extract prepared by the preparation method as an active ingredient, wherein the enzyme-treated Zizania latifolia Turcz. extract contains 0.01% to 90% by weight of tricin.

The health functional food composition may be used for whitening, wrinkle improvement, inflammation improvement, allergy improvement or moisturizing, and contains a high content of tricin, thereby exhibiting excellent whitening, wrinkle improvement, inflammation improvement, allergy improvement and moisturizing effect.

In the present invention, the term "health functional food" refers to food manufactured and processed using ingredients or components having functional properties useful for the human body according to Act No. 6727 of the Health Functional Food, and "functional" means ingestion for the purpose of obtaining useful effects for health purposes such as controlling nutrients or physiological effects on the structure and function of the human body.

The health functional food composition may further include conventional food additives and it suitability as a "food additive" is determined by the standards for the relevant item in accordance with General Regulations and General Test Methods of Korean Food Additives Codex approved by the Ministry of Food and Drug Safety, unless otherwise specified.

Examples of the items published in the above-mentioned "Korean Food Additives Codex" include chemical synthetics such as ketones, glycine, potassium citrate, nicotinic acid, and cinnamic acid and the like, natural additives such as persimmon extract, licorice extract, crystalline cellulose, kaoliang color and guar gum and the like, mixed preparations such as L-sodiumglutamate preparation, alkaline agents for noodles, preservative formulation and a tar color formulation and the like.

The composition of the present invention can be variously used in food and beverages for improving skin whitening, moisturizing, anti-allergy, wrinkles, for example, various foods, beverages, gums, teas, vitamin complexes, health functional supplements, food additives, and it may be used in the form of a powder, granule, tablet, capsule, pill or beverage, and may be any food form other than those described above.

The formulation of the food composition of the present invention is prepared according to a conventional method, dried with a carrier, and then encapsulated or can be formulated in the form of other tablets, granules, powders, beverages, porridges, etc. and It is possible to prepare all food forms other than those described above.

The food composition of the present invention may contain an active ingredient in an amount of 0.001 to 100 parts by weight based on 100 parts by weight of the composition. However, the content of the active ingredient is not limited thereto, and may be appropriately adjusted, and may be used in an amount above the above range.

Hereinafter, the present invention will be described in more detail through examples. These examples are only intended to illustrate the present invention in more detail, and it will be apparent to those skilled in the art that the scope of the present invention is not limited by these examples according to the gist of the present invention.

Preliminary Experiment

<Preliminary Experiment 1> Optimization of Ethanol Extraction Process of Zizania Latifolia Turcz 1.1) After weighing 50 g of commercially available Zizania latifolia Turcz., times the weight of 10, 30, 50, 70, 90 w/w % fermented ethanol was added, extraction was carried out at 80° C. for 6 hours, and filtered to obtain ethanol extract of Zizania latifolia Turcz.

The ethanol extract of Zizania latifolia Turcz. was concentrated and dried to obtain ethanol extract powder, and the weight of the extract solid according to the ethanol concentration ratio was measured, and the tricin content and the inhibitory effect of NO generation were confirmed.

Specifically, the content of tricin was confirmed as follows: HPLC (Agilent 1260) was used as an analyzer, and Discovery C18, C-18, 5 μm, 250×4.6 mm (SUPELCO) was used as an analytical column. When preparing the standard, 2 mg of the tricin standard was weighed, and methanol for HPLC was added to make 20 mL for the standard stock solution and using the standard stock solution, a standard product of the linear section was prepared at concentrations of 1, 3, 5, 10, and 20 ppm.

When preparing the test solution, 100 mg of the Zizania latifolia Turcz. extract prepared in Preliminary Experiments 1 and 2 was weighed and placed in a 50 mL volumetric flask, and half of methanol was added to perform sonification for 30 minutes. After the treatment was completed, the mark was aligned, vortexed, and filtered through a 0.45 μm membrane filter to obtain a test solution.

At this time, the analysis method was as shown in the following <Table 1>.

TABLE 1

| Column Temp. Flow rate | Discovery: C18(4.6 × 250 mm, 5 μm) 80° C. 1.0 ml/min | | |
|---|---|---|---|
| Mobile phase | A = 0.15% $H_3PO_4$ inDW, B = Mathanol | | |
| | Time (min) | A (%) | B (%) |
| | 0 | 80 | 20 |
| | 3 | 80 | 20 |
| | 3.1 | 50 | 50 |
| | 8 | 50 | 50 |
| | 8.1 | 45 | 55 |
| | 20 | 45 | 55 |
| | 30.1 | 15 | 85 |
| | 30 | 15 | 86 |

TABLE 1-continued

|  | 30.1 | 80 | 20 |
|---|---|---|---|
|  | 45 | 80 | 20 |
| Detector |  | DAD (350 nm) |  |
| Injection volume |  | 10 μL |  |

The production of NO was confirmed through the NO assay, and the specific process was as follows: The macrophage cell line RAW264.7 was distributed from the Korea Cell Line Bank (KCLB, Seoul, Korea), and using DMEM medium (Welgene, Gyeongsan, Korea) to which 10% FBS and 1% antibiotics (penicillin/streptomycin) were added, the cells were subcultured 2 to 3 times in an incubator at 37° C. in the presence of 5% $CO_2$ and used.

RAW264.7 cells were dispensed into a 96-well plate at $1 \times 10^6$ cells/well and pre-cultured in a 5% $CO_2$ incubator for 20 to 24 hours, and each extract sample was treated and cultured for 24 hours. 10 μL of lipopolysaccharide (Sigma-Aldrich, USA) at a concentration of 1 mg/mL was injected into each well to induce inflammation of the macrophage cell line RAW264.7 cells. Thereafter, 100 μL of the supernatant was transferred to a 96-well plate and 100 μL of Griess reagent containing 2.5% phosphoric acid, 1% sulfanylamide and 0.1% N-(1-naphthyl)ethylenediamine was added to each well for reaction. After the reaction was completed, optical density (O.D) was measured with an ELISA reader at a wavelength of 540 nm. At this time, the measured O.D was expressed as a percentage (%) compared with the O.D value in the cells to which lipopolysaccharide was added.

The results were shown in Table 2 below.

TABLE 2

| Extraction solvent | Extract solids (g) | Tricin content (mg/g) | NO production | |
|---|---|---|---|---|
|  |  |  | (μg/ml) | Inhibition (%) |
| 10% EtOH extraction | 6.45 | — | 100 | 2.56 |
|  |  |  | 250 | 32.78 |
|  |  |  | 500 | 46.20 |
| 30% EtOH extraction | 6.46 | 0.6068 | 100 | 32.90 |
|  |  |  | 250 | 39.48 |
|  |  |  | 500 | 58.30 |
| 50% EtOH extraction | 6.73 | 0.7709 | 100 | 20.78 |
|  |  |  | 250 | 49.18 |
|  |  |  | 500 | 87.89 |
| 70% EtOH extraction | 6.80 | 1.2738 | 100 | 57.67 |
|  |  |  | 250 | 65.54 |
|  |  |  | 500 | 81.76 |
| 90% EtOH extraction | 4.84 | 0.9109 | 100 | 35.05 |
|  |  |  | 250 | 56.77 |
|  |  |  | 500 | 86.61 |

Referring to Table 2, it was confirmed that the yield was the highest in the 70% ethanol extract. Tricin was not found in the 10% ethanol extract, and the highest content was 70% ethanol extract. As a result of confirming the amount of NO production, at 100 and 250 μg/ml, the 70% ethanol extract had the best inhibitory effect on NO production, and at 500 μg/ml, the 50% ethanol extract showed better results. By combining the above results, a 70% ethanol solvent exhibiting high activity at low concentration while having high yield and tricin content was determined as the optimal extraction solvent.

1.2) In order to check the effect according to the change of extraction time, after weighing 50 g of Zizania latifolia Turcz., 70 w/w % fermented ethanol of 20 times the weight was added and extracted for 2, 4, 6, 8 hours at 80° C. and filtered to obtain an ethanol extract of Zizania latifolia Turcz.

The ethanol extract of Zizania latifolia Turcz. was concentrated and dried to obtain the ethanol extract powder, and the content of tricin and the amount of inhibition of NO generation were confirmed as described above, and the results were shown in Table 3 below.

TABLE 3

| Extraction time | Extract solids (g) | Tricin content (mg/g) | NO production | |
|---|---|---|---|---|
|  |  |  | (μg/ml) | Inhibition (%) |
| 2 hours | 6.02 | 0.3016 | 100 | 23.71 |
|  |  |  | 250 | 37.58 |
|  |  |  | 500 | 49.43 |
| 4 hours | 6.49 | 0.6624 | 100 | 23.37 |
|  |  |  | 250 | 38.32 |
|  |  |  | 500 | 71.74 |
| 6 hours | 6.80 | 1.2738 | 100 | 57.67 |
|  |  |  | 250 | 65.54 |
|  |  |  | 500 | 81.76 |
| 8 hours | 6.95 | 0.9282 | 100 | 32.57 |
|  |  |  | 250 | 56.45 |
|  |  |  | 500 | 79.73 |

Referring to Table 3, the yield at the time of extraction for 8 hours was the highest, but the content of tricin was highest at the time of extraction for 6 hours. In the NO production inhibitory effect, it was found to be high at all concentrations when extracted for 6 hours.

From the above results, the yield was high when extracted for 8 hours, but the difference from 6 hours was insignificant, so the extraction for 6 hours showing the higher tricin content and high activity at all concentrations was determined as the optimum extraction time.

1.3) In order to check the effect according to the temperature, after weighing 50 g of Zizania latifolia Turcz., 70 w/w % fermented ethanol of 20 times the weight was added and extracted at 60, 80° C. for 6 hours and filtered to obtain an ethanol extract of Zizania latifolia Turcz. The ethanol extract of Zizania latifolia Turcz. was concentrated and dried to obtain the ethanol extract powder. Thereafter, the extract solid content, tricin content and NO production inhibitory effect were checked in the same manner as described above, and the results were shown in Table 4 below.

TABLE 4

| Extraction temperature | Extract solids (g) | Tricin content (mg/g) | NO production | |
|---|---|---|---|---|
|  |  |  | (μg/ml) | Inhibition (%) |
| 60° C. | 6.14 | 0.4136 | 100 | 40.45 |
|  |  |  | 250 | 60.06 |
|  |  |  | 500 | 74.20 |
| 80° C. | 6.80 | 1.2738 | 100 | 57.67 |
|  |  |  | 250 | 65.54 |
|  |  |  | 500 | 81.76 |

Referring to <Table 4>, it was confirmed that the extraction yield and tricin content at 80° C. were higher than those extracted at 60° C. In addition, as a result of confirming the NO production inhibitory effect, the extract was high at 80° C. in all of 100, 250, and 500 μg/ml. By combining these results, the extraction at 80° C., which showed high yield and high tricin content and high activity at all concentrations, was determined as the optimum extraction temperature.

All results of the above extraction solvent, extraction time, and extraction temperature were collected, and the final extraction process was determined as 70% ethanol, 6 hours, and 80° C.

<Preliminary Experiment 2> Preparation of Ethanol Extract of Zizania *Latifolia* Turcz After weighing 1 kg of Zizania *latifolia* Turcz., 20 times the weight of 70 w/w % fermented ethanol was added, extracted at 80° C. for 6 hours, and then filtered to obtain an ethanol extract of Zizania *latifolia* Turcz. The ethanol extract of Zizania *latifolia* Turcz. was concentrated and dried to obtain an ethanol extract powder of Zizania *latifolia* Turcz.

<Preliminary Experiment 3> Enzyme Selection Experiment of Enzyme-Treated Extract of Zizania *Latifolia* Turcz After weighing 100 g of Zizania *latifolia* Turcz., purified water of 20 times the weight was added and extracted at 80° C. for 1 hour. After enzyme treatment of it with pectinase, cellulase, hemicellulase, tannase, α-amylase, β-glucosidase under the conditions shown in the following <Table 5>, the first filtration was performed to obtain the first enzyme-treated extract of Zizania *latifolia* Turcz. Each condition was set as the optimum condition for the enzyme.

TABLE 5

|  | Temperature (° C.) | pH | Input amount | Treatment time (hr) |
| --- | --- | --- | --- | --- |
| pectinase | 25 | 4.0 | 0.75 ml (%) | 24 hours |
| cellulase | 37 | 5.0 | 1 g (%) | 24 hours |
| hemicellulase | 40 | 4.5 | 1 g (%) | 24 hours |
| tannase | 40 | 4.5 | 1 g (%) | 24 hours |
| a-amylase | 60 | 6.5 | 1.5 ml (%) | 24 hours |
| β-glucosidase | 40 | 4.5 | 1 g (%) | 24 hours |

After the first filtration, 10 times of 70 w/w % fermented ethanol was added to the remaining residue, ethanol extraction was performed at 80° C. for 4 hours, and the second filtration was performed to obtain a second ethanol extract of Zizania *latifolia* Turcz. The first enzyme-treated extract of Zizania *latifolia* Turcz. and the second enzyme-treated extract of Zizania *latifolia* Turcz. were mixed, and concentration and drying were performed and finally, an extract powder of the enzyme-treated extract of Zizania *latifolia* Turcz. was obtained.

<Preliminary Experiment 4> Preparation of Mixed Enzyme-Treated Extract of Zizania *Latifolia* Turcz Two or more kinds of enzymes from four kinds of enzymes of β-glucosidase, pectinase, cellulase, and hemicellulose were mixed and treated to prepare an enzyme-treated extract. After weighing 100 g of Zizania *latifolia* Turcz. extract, purified water of 20 times the weight was added to hot water extract at 80° C. for 1 hour. Various ratios of enzymes were mixed by adding at the ratio specified below relative to the input amount of the raw material of the Zizania *latifolia* Turcz. and after the enzyme treatment according to the conditions shown in <Table 6> below, the first filter was performed to obtain a first extract of the enzyme-treated of Zizania *latifolia* Turcz. extract.

1) 0.5% by weight of pectinase: 0.5% by weight of cellulase
2) 0.5% by weight of pectinase: 0.5% by weight of hemicellulase
3) 0.5% by weight of cellulase: 0.5% by weight of hemicellulose
4) 0.33% by weight of pectinase: 0.33% by weight of cellulase: 0.33% by weight of hemicellulase
5) 0.33% by weight of β-glucosidase: 0.33% by weight of cellulase: 0.33% by weight of hemicellulose At this time, the input amount of each enzyme is a comparison amount to the input amount of the raw material of Zizania *latifolia* Turcz.

TABLE 6

|  | Temperature (° C.) | pH | Input amount | Treatment time (hr) |
| --- | --- | --- | --- | --- |
| 1) mixed enzyme | 30 | 4.5 | 0.5%:0.5% | 24 |
| 2) mixed enzyme | 35 | 4.5 | 0.5%:0.5% | 24 |
| 3) mixed enzyme | 40 | 4.5 | 0.5%:0.5% | 24 |
| 4) mixed enzyme | 35 | 4.5 | 0.33%:0.33%:0.33% | 24 |
| 5) mixed enzyme | 40 | 4.5 | 0.33%:0.33%:0.33% | 24 |

After the first filtration, 10 times of 70 w/w % fermented ethanol was added to the remaining residue, ethanol extraction was performed at 80° C. for 4 hours, and the second filtration was performed to obtain a second ethanol extract of Zizania *latifolia* Turcz. The first enzyme-treated extract of Zizania *latifolia* Turcz. and the second enzyme-treated extract of Zizania *latifolia* Turcz. were mixed, and concentration and drying were performed and finally, an extract powder of the enzyme-treated extract of Zizania *latifolia* Turcz. was obtained.

<Preliminary Experiment 5> Confirmation of Yield of Zizania *Latifolia* Turcz. Extract and Tricin Content The tricin content of the Zizania *latifolia* Turcz. extract prepared in the above Preliminary Experiments 2 to 4 was compared and analyzed. As the analyzer, HPLC (Agilent 1260) was used, and as the analytical columns, Discovery C18, C-18, 5 μm, 250×4.6 mm (SUPELCO) was used.

When preparing the standard, 2 mg of the tricin standard was weighed, and methanol for HPLC was added to make 20 mL for the standard stock solution and using the standard stock solution, a standard product of the linear section was prepared at concentrations of 1, 3, 5, 10, and 20 ppm.

When preparing the test solution, 100 mg of the Zizania *latifolia* Turcz. extract prepared in Preliminary Experiments 1 and 2 was weighed and placed in a 50 mL volumetric flask, and half of methanol was added to perform sonification for 30 minutes. After the treatment was completed, the mark was aligned, vortexed, and filtered through a 0.45 μm membrane filter to obtain a test solution.

At this time, the analysis method was as shown in Table 1 above.

As a result, as shown in FIG. 2, it was confirmed that the yield of each enzyme-treated extract was higher than that of the ethanol extract.

In addition, as shown in FIG. 3, it was confirmed that the tricin content of the extract treated with a mixture of β-glucosidase, cellulase, and hemicellulase was higher than that of the ethanol extract of Zizania latifolia Turcz.

On the other hand, FIG. 4 shows the tricin chromatogram of the ethanol extract and the chromatogram of the extract of Zizania latifolia Turcz. treated with enzyme mixture of β-glucosidase, cellulase and hemicellulose and it can be seen that the tricin content is increased when the mixed enzyme is treated, and the peaks of the tricin glycosides in the front part are reduced compared to the ethanol extract. It can be indirectly confirmed that the content of tricin increases due to the decrease of tricin glycosides and derivatives.

Based on the above results, the total amount of tricin in consideration of the yield of ethanol extract and enzyme-treated extract of Zizania latifolia Turcz. was shown in a graph of FIG. 5.

<Preliminary Experiment 6> Confirmation of Anti-Inflammatory Efficacy of Zizania Latifolia Turcz. Extract The anti-inflammatory effect of the extract of Zizania latifolia Turcz. prepared in the above Preliminary Experiments 2 to 4 was confirmed. The macrophage cell line RAW264.7 was distributed from the Korea Cell Line Bank (KCLB, Seoul, Korea), and using DMEM medium (Welgene, Gyeongsan, Korea), the cells were subcultured 2 to 3 times in an incubator at 37° C. in the presence of 5% $CO_2$ and used.

Thereafter, an MTT assay was performed to measure the cell viability of the RAW264.7 sample. RAW264.7 cells were dispensed into a 96-well plate at $1\times10^6$ cells/well and pre-incubated in a 5% $CO_2$ incubator for 20 to 24 hours, and each extract sample was treated and cultured again for 24 hours, and then 10 μL of MTT (5 mg/mL) solution dissolved in PBS was added to each well and reacted in an incubator for 4 hours. Then, the supernatant was removed, and 100 μL of DMSO was added to each well to dissolve the resulting formazan crystal, and the absorbance was measured with an ELISA reader at 550 nm wavelength. The degree of formazan production measured in this way was expressed as a percentage (%) compared to the value of normal cells.

Second, NO assay was performed to measure the anti-inflammatory effect of the Zizania latifolia Turcz. extract and tricin using RAW264.7. First, RAW264.7 cells were dispensed into a 96-well plate at $1\times10^6$ cells/well and pre-cultured in a 5% $CO_2$ incubator for 20 to 24 hours, and each extract sample was treated and cultured for 24 hours. 10 μL of lipopolysaccharide (Sigma-Aldrich, USA) at a concentration of 1 mg/mL was injected into each well to induce inflammation of the macrophage cell line RAW264.7 cells. Thereafter, 100 μL of the supernatant was transferred to a 96-well plate and 100 μL of Griess reagent containing 2.5% phosphoric acid, 1% sulfanylamide and 0.1% N-(1-naphthyl)ethylenediamine was added to each well for reaction. After the reaction was completed, optical density (O.D) was measured with an ELISA reader at a wavelength of 540 nm. At this time, the measured O.D was expressed as a percentage (%) compared with the O.D value in the cells to which lipopolysaccharide was added.

As a positive control, RAW264.7 cells to which lipopolysaccharide was not added were used, and as a negative control, cells to which Lω-nitro-L-arginine methyl ester (L-NAME, Sigma-Aldrich, USA) acting as an NO inhibitor was added were used.

As a result, as shown in FIG. 6, it was confirmed that the anti-inflammatory efficacy of the extract treated with a mixture of β-glucosidase, cellulase and hemicellulase was superior to that of the ethanol extract at the sample treatment concentration of 500 μg/ml.

<Preliminary Experiment 7> Confirmation of Whitening Effect of Zizania Latifolia Turcz. Extract The whitening effect of the Zizania latifolia Turcz. extract prepared in the above Preliminary Experiments 2 to 4 was confirmed. First, mouse-derived melanin cell line B16-F0 cells were distributed from the American Type Culture Collection (ATCC, USA), and using DMEM medium (ATCC, ATCC 30-2002, USA) to which 10% FBS and 1% antibiotics (penicillin/streptomycin) were added, the cells were subcultured 2 to 3 times in an incubator at 37° C. in the presence of 5% $CO_2$ and used.

Thereafter, an MTT assay was performed to measure the cell viability for the sample of B16-F0 cells. B16-F0 cells were dispensed into a 24-well plate at $5\times10^5$ cells/well and pre-cultured in a 5% $CO_2$ incubator for 20 to 24 hours, and each extract sample was treated and cultured for 48 hours, and then 100 μL of MTT solution (5 mg/mL) dissolved in PBS was added to each well and reacted in an incubator for 4 hours. Thereafter, the supernatant was removed, and 500 μL of DMSO was added to each well to dissolve the resulting formazan crystal, and the absorbance was measured with an ELISA reader at 550 nm wavelength. The measured degree of formazan production was expressed as a percentage (%) compared to the value of normal cells.

Second, the ability of the Zizania latifolia Turcz. extract and tricin to inhibit melanin production in the mouse-derived melanin cell line B16-F0 was measured. B16-F0 cells were dispensed into a 6-well plate at $5\times10^5$ cells/well and pre-cultured in a 5% $CO_2$ incubator for 20 to 24 hours, and then each extract sample was treated and cultured for 48 hours. At this time, DMEM medium containing 1 μM α-melanocyte stimulating hormone (Sigma-Aldrich, USA) and 100 μM 3-isobutyl-1-methylxanthine (Sigma-Aldrich, USA) was used to promote melanin production along with sample treatment. After completion of the culture, the supernatant was removed, and 1,000 μL of warm PBS solution was added to each well, followed by incubation at 37° C. for 10 minutes.

The melanoma cells adhered to the surface of the 6-well plate were removed from the cultured cells, dispensed into a 1.5 mL tube, and centrifuged at 13,000 rpm for 10 minutes using a centrifuge maintained at 4° C. After centrifugation, the supernatant was carefully removed and 150 μL of a lysis solution (1.0 N NaOH: dimethyl sulfoxide=9:1) was added to dissolve melanin. After reacting for 1 hour in an oven at 60° C., 100 μL was dispensed to each well in a 96-well plate and O.D was measured with an ELISA reader (405 nm). As a control, O.D from melanoma cells not reacted with the sample was used. In addition, 250 uM arbutin (Sigma-Aldrich, USA) having melanin inhibitory ability through inhibition of tyrosinase production was used as a negative control.

As a result, as shown in FIG. 8, it was confirmed that the whitening effect of the extract treated with a mixture of β-glucosidase, pectinase, cellulase, and hemicellulase was superior to that of the ethanol extract of Zizania latifolia Turcz. at the sample treatment concentration of 500 μg/ml.

<Preliminary Experiment 8> Confirmation of Anti-Wrinkle Effect of Zizania *Latifolia* Turcz. Extract The anti-wrinkle effect of the *Zizania latifolia* Turcz. extract prepared in Preliminary Experiments 2 to 4 was confirmed. First, human-derived CCD-986sk fibroblast cells were distributed from Korea Culture Tissue Collection (KCTC, Korea), and human dermal fibroblasts (HDF) were distributed from Seorin Bio. In addition, CCD-986sk fibroblasts were subcultured 2 to 3 times in an incubator at 37° C. in the presence of 5% $CO_2$ using IMDM medium (ATCC, ATCC 30-2005, USA) supplemented with 10% FBS and 1% antibiotics (penicillin/streptomycin) and used. HDF was subcultured 2 to 3 times using a special HDF medium (Cellbio, Korea) supplemented with 10% FBS and 1% antibiotic (penicillin/streptomycin) and used.

Thereafter, MTT assay was performed to measure the cell viability for the samples of CCD-986sk cells and HDF. Specifically, CCD-986sk cells and HDF were dispensed into a 96-well plate at $1\times10^5$ cells/well, pre-cultured in a 5% $CO_2$ incubator for 20 to 24 hours, and each extract sample was treated and cultured for 24 hours, and then 10 μL of a solution of MTT (5 mg/mL) dissolved in PBS was added to each well and reacted in an incubator for 4 hours. Thereafter, the supernatant was removed, and 100 μL of DMSO was added to each well to dissolve the resulting formazan crystal, and the absorbance was measured with an ELISA reader at 550 nm wavelength. The measured degree of formazan production was expressed as a percentage (%) compared to the value of normal cells.

Second, procollagen and MMP families (MMP-1, 2, 3, 9, 13) are factors that are discharged to the outside of the cell culture solution, and the cell culture solution reacted with the sample was collected and used. That is, in order to measure the ability to synthesize procollagen for tricin and enzyme treatment of *Zizania latifolia* Turcz. (standard sample), procollagen type I C-peptide EIA kit manufactured by Takara was used, the quantification curve was measured using PIP to calculate the amount of collagen synthesis for each sample. In addition, by measuring the inhibitory ability of metalloproteinase-1 (MMP-1), MMP-2, MMP-3, MMP-9, and MMP-13, which are factors affecting wrinkles, *Zizania latifolia* Turcz. enzyme treatment (standard sample) and tricin were evaluated for wrinkle improvement effect. The inhibitory ability of MMP-1, 2, 3, 9, 13 was measured using a product manufactured by Abcam.

As a result, as shown in FIG. 10, it was confirmed that the anti-wrinkle effect of the extract treated with a mixture of β-glucosidase, pectinase, cellulase, and hemicellulase was superior to that of the ethanol extract of *Zizania latifolia* Turcz. at the sample treatment concentration of 500 μg/ml.

<Preliminary Experiment 9> Confirmation of Anti-Allergic Efficacy of *Zizania latifolia* Turcz. Extract The anti-allergic efficacy of the *Zizania latifolia* Turcz. extract prepared in the above Preliminary Experiments 2 to 4 was confirmed. First, RBL-2H3 cells, a rat basophilic leukemia cell line, were purchased from Korea Cell Line Bank (KCLB, Seoul, Korea). RBL-2H3 cells were cultured in MEM (Gibco BRL, NY, USA) medium containing 10% FBS and 1% penicillin/streptomycin in an incubator at 37° C. and 5% CO.

First, in order to confirm the cytotoxicity of the sample, MTT analysis was performed to analyze the active mitochondria reducing the penetrated formazan dye to MTT to confirm the cell viability. RBL-2H3 cells were dispensed into a 96-well plate at $3\times10^4$ cells per well, and the following day, the *Zizania latifolia* Turcz. extract was treated at 37° C. After 48 hours, 100 μL of MTT (5 mg/mL) was added to each well and incubated at 37° C. for 4 hours. Then, 100 μL of DMSO was added to each well to lyse the cells. The plate was maintained at room temperature for 5 minutes and absorbance was measured at 550 nm using a multiwell spectrophotometer (Molecular Devices, Sunnyvale, CA).

Second, the inhibitory effect of the extract on the release of β-hexosaminidase was confirmed in RBL-2H3 cells. RBL-2H3 cells were dispensed into a 24-well plate at $2\times10^5$ cells per well and stimulated with anti-DNP IgE (450 ng/mL) overnight at 37° C. Thereafter, the cells were washed with Siraganian buffer, 160 μL of incubation buffer was added, and incubated at 37° C. for 20 minutes, and then 20 μL of the extract sample was treated to the cells for 10 minutes and 20 μL of antigen (DNP-BSA, 10 μg/mL) was added to stimulate the cells to form granules at 37° C. for 10 minutes. Then, the reaction was stopped by immersing in an ice water bath for 10 minutes. 25 μL of the supernatant was transferred to a 96-well plate and 25 μL of 0.1 M citrate buffer (pH 4.5) in which the substrate (1 mM p-nitrophenyl-nacetyl-β-D-glucosaminide) is dissolved, was added and reacted at 37° C. for 1 hour. Thereafter, 200 μL of a stop solution (0.1 M $Na_2CO_3$/$NaHCO_3$, pH 10.0) was added to stop the reaction, and the absorbance was measured at 405 nm using a microplate reader.

Third, IL-4 and TNF-α are cytokines released to the outside of cells, and cell culture media were collected and used after performing the same experimental method, and IL-4 and TNF-α were measured by using Abcam and R&D systems kits as ELISA techniques according to the manual.

As a result, as shown in FIG. 12, it was confirmed that the anti-allergic efficacy of the extract treated with a mixture of β-glucosidase, pectinase, cellulase, and hemicellulase was superior to that of the ethanol extract of *Zizania latifolia* Turcz. at the sample treatment concentration of 500 μg/ml.

Example

<Example 1> Preparation of Mixed Enzyme-Treated Extract of *Zizania latifolia* Turcz After weighing 1 kg of *Zizania latifolia* Turcz., 20 times the weight of purified water was added to extract hot water at 80° C. for 1 hour. β-glucosidase, cellulase, and hemicellulase enzymes purchased in the market of 1.0 w/w % of the weight of the *Zizania latifolia* Turcz. were added to it, subjected to enzymatic treatment at 35° C. for 24 hours, and then followed by the first filtration to obtain a first enzyme-treated *Zizania latifolia* Turcz. extract.

After the first filtration, 10 times the amount of 70 w/w % fermented alcohol was added to the remaining residue, followed by ethanol extraction at 80° C. for 4 hours and the secondary filtration to obtain a second ethanol extract of the *Zizania latifolia* Turcz. The first enzyme-treated *Zizania latifolia* Turcz. extract and the secondary ethanol extract of *Zizania latifolia* Turcz. were mixed, concentrated and dried, and finally, an powder of enzyme-treated *Zizania latifolia* Turcz. extract was obtained. The optimal conditions of the enzyme treatment extraction process were set by performing the process of Preliminary Experiments 3 to 10.

Comparative Example

<Comparative Example 1> Preparation of Ethanol Extract of *Zizania latifolia* Turcz After weighing 1 kg of *Zizania latifolia* Turcz., 70 w/w % fermented alcohol of 20 times the weight was added, extracted at 80° C. for 6 hours, and filtered to obtain an ethanol extract of *Zizania latifolia* Turcz. The ethanol extract of *Zizania latifolia* Turcz. was concentrated and dried to obtain powder of ethanol extract of *Zizania latifolia* Turcz.

The ethanol extraction process is a method of ethanol extraction of *Zizania latifolia* Turcz. as mentioned in several papers or patents, and optimal conditions were set through Preliminary Experiment 1.

Experimental Example

<Experimental Example 1> Material Separation and Tricin Confirmation

According to HPLC analysis, it was found that the enzyme-treated *Zizania latifolia* Turcz. extract contained a large amount of tricin. Accordingly, the following experiment was performed to determine whether tricin was contained in the enzyme-treated *Zizania latifolia* Turcz. extract by investigating the separation and structure of the substance.

The method of separating the tricin material was as follows: (1) 5 kg of the dried powder of enzyme-treated *Zizania latifolia* Turcz. extract was extracted in 45 L of 80% methanol at room temperature. (2) The concentrated solution of (1) was subjected to three fractions of EtOAc 3L, 3 times and n-BuOH 3L, 3 times. (3) The EtOAc fraction of (2) was named as ZLE, the n-BuOH fraction was named as ZLB, and the remaining extract after fractionation was named as ZLW. (4) The ZLE extract was fractionated in each solvent condition from $CHCl_3$:MeOH 50:1 to 1:1 using a silica gel-filled normal phase column to obtain fractions from ZLE-1 to ZLE-13. (5) In the fraction of (4), ZLE-8 was subjected to each fraction using prep-LC, and the separated fractions were named as ZLE-8-1 to ZLE-8-14. (6) From the fraction of (5) above, the fraction of ZLE-8-4 was separated by using prep-LC under the following conditions.

Mobile phase=A: water and 0.1% formic acid
B: acetonitrile and 0.1% formic acid
Concentration gradient=0.5%/min from 10% B to 35% B 0.6%/min from 35% B to 60% B (7) Each single substance was obtained under the condition of (6), and as a result of structural analysis, it was confirmed that it was tricin.

<Experimental Example 2> Confirmation of Anti-Inflammatory Efficacy of Tricin The experiment was carried out in the same manner as described in the anti-inflammatory efficacy test method in Preliminary Experiment 7.

As a result, as shown in FIG. 7, it was confirmed that the NO generation according to the concentration of a single substance tricin decreased in a concentration-dependent manner, which suggests that the efficacy changes according to the content of tricin in the enzyme treatment of *Zizania latifolia* Turcz.

<Experimental Example 3> Confirmation of Whitening Efficacy of Tricin

The experiment was performed in the same manner as the whitening efficacy test method in Preliminary Experiment 8.

As a result, as shown in FIG. 9, it was confirmed that the melanin generation according to the concentration of a single substance tricin decreased in a concentration-dependent manner, which suggests that the efficacy changes according to the content of tricin in the enzyme treatment of *Zizania latifolia* Turcz.

<Experimental Example 4> Confirmation of Wrinkles Improvement Efficacy of Tricin The experiment was performed in the same manner as the wrinkles improvement efficacy test method in Preliminary Experiment 9.

As a result, as shown in FIG. 11, it was confirmed that the collagen generation according to the concentration of a single substance tricin increased in a concentration-dependent manner, which suggests that the efficacy changes according to the content of tricin in the enzyme treatment of *Zizania latifolia* Turcz.

<Experimental Example 5> Confirmation of Anti-Allergic Efficacy of Tricin

The experiment was performed in the same manner as the wrinkles improvement efficacy test method in Preliminary Experiment 10.

As a result, as shown in FIG. 13, it was confirmed that the β-hexosaminidase release rate according to the concentration of a single substance tricin decreased in a concentration-dependent manner, which suggests that the efficacy changes according to the content of tricin in the enzyme treatment of *Zizania latifolia* Turcz.

<Experimental Example 6> Comparison of Yield and Tricin Content of Ethanol Extract and Enzyme-Treated Extract of *Zizania latifolia* Turcz The results of comparing the yields of the extracts prepared in Example 1 and Comparative Example 1 were shown in FIG. 23.

As a result of comparing the extract yield, as shown in FIG. 23, the yield of the extract extracted with the mixed enzyme of β-glucosidase, cellulase and hemicellulase was 21.37%, which was more than twice as high as 10.96% of the ethanol extract of *Zizania latifolia* Turcz. and thus it was confirmed that the commercial utilization value was higher.

The content of tricin of the extracts prepared in Example 1 and Comparative Example 1 was analyzed. At this time, the experiment was performed in the same manner as the tricin content analysis method in Preliminary Experiment 6.

As a result, as shown in FIG. 24, the tricin content of the extract of *Zizania latifolia* Turcz. treated with the mixed enzyme of β-glucosidase, cellulase and hemicellulase was 3.31 mg/g, which was increased by about 2.6 times of 1.27 mg/g of ethanol extract of *Zizania latifolia* Turcz.

When the above results were compared in terms of the recovery rate of tricin compared to the raw material of the *Zizania latifolia* Turcz., it was confirmed that the recovery rate of tricin was 139.2 mg/kg in the case of the simple extract of alcohol, and the recovery rate of tricin when treated with the complex enzyme was 707.3 mg/kg, which was increased by 5.08 times.

<Experimental Example 7> Confirmation of Anti-Inflammatory Efficacy of Ethanol Extract and Enzyme-Treated Extract of *Zizania latifolia* Turcz Anti-inflammatory efficacy of the extracts prepared in Example 1 and Comparative Example 1 was evaluated. At this time, the experiment was performed in the same manner as the anti-inflammatory efficacy test method in Preliminary Experiment 7.

As a result, as shown in FIG. 25, the NO production amount of the extract of *Zizania latifolia* Turcz. treated with the mixed enzyme of β-glucosidase, cellulase and hemicellulase was 17.89 μM, which was reduced by 8.41 μM from 26.3 μM (ethanol extract of *Zizania latifolia* Turcz.).

<Experimental Example 8> Confirmation of Whitening Efficacy of Ethanol Extract and Enzyme-Treated Extract of *Zizania latifolia* Turcz The whitening efficacy of the extracts prepared in Example 1 and Comparative Example 1 was evaluated. The experiment was performed in the same manner as the whitening effect test method in Preliminary Experiment 8.

As a result, as shown in FIG. 26, the melanin production rate of the extract of *Zizania latifolia* Turcz. treated with the mixed enzyme of β-glucosidase, cellulase and hemicellulase was 47.989%, which was reduced by 20.334% from 68.323% of the ethanol extract of *Zizania latifolia* Turcz.

<Experimental Example 9> Confirmation of Anti-Wrinkle Efficacy of Ethanol Extract and Enzyme-Treated Extract of *Zizania latifolia* Turcz The wrinkle improvement efficacy of the extracts prepared in Example 1 and Comparative Example 1 was evaluated. The experiment was performed in the same manner as the wrinkle improvement efficacy test method in Preliminary Experiment 9.

As a result, as shown in FIG. 27, the collagen synthesis amount of the extract of *Zizania latifolia* Turcz. treated with the mixed enzyme of β-glucosidase, cellulase and hemicellulase was 9803.6093 ng/ml, which was increased by 2401.4996 ng from 7402.1097 ng/ml of the ethanol extract of *Zizania latifolia* Turcz.

<Experimental Example 10> Confirmation of Anti-Allergic Efficacy of Ethanol Extract and Enzyme-Treated Extract of *Zizania latifolia* Turcz The anti-allergic efficacy of the extracts prepared in Example 1 and Comparative Example 1 was evaluated. The experiment was performed in the same manner as the anti-allergic efficacy test method in Preliminary Experiment 10.

As a result, as disclosed in FIG. 28, the β-hexosaminidase release rate of the extract treated with the mixed enzyme of β-glucosidase, cellulase and hemicellulase was 7.45%, which was reduced by 11.57% from 19.02% of the ethanol extract of *Zizania latifolia* Turcz.

<Experimental Example 11> Confirmation of Anti-Wrinkle and Moisturizing Efficacy Through Animal Testing of Mixed Enzyme-Treated Extract of *Zizania latifolia* Turcz 1. Experimental Method The anti-wrinkle improvement and moisturizing effects were confirmed through animal experiments for the enzyme-treated extract of *Zizania latifolia* Turcz. prepared in the above Example 1. For the experiment, biochemical analysis equipment (Roche Ltd, Basel, Switzerland), glass teflon homogenizer (Chang shin scientific Co., Korea), microplate reader (Bio-TEK, USA), protein quantification equipment (Chemi-Doc; BIORAD, USA), a centrifuge (Hanil FLETA5, Korea), a water bath (Thermo minder taitec, Japan), and a deep freezer (Sanyo, Japan) were used. In addition, glass Teflon homogenizer (Daihan Scientific Group, Korea), UV-spectrophotometer (Shimadzu UV-1201, Japan), high-speed centrifuge (Hanil HMR-1610V, Korea), medical freezer (Sanyo, Japan)), a microplate reader (Bio-TEK), and protein quantification equipment (Chemi-Doc; BIORAD) were used.

The SKH-1 hairless mouse type, 6-week-old model (female) used in this experiment was imported and distributed from Orient Bio (Seongnam, Gyeonggi-do, Korea), and after a week of quarantine and acclimated breeding in the animal house of Southeast Medi-Chem Institute (animal facility registration certificate: No. 412), a specific breeding environment for healthy animals (temperature (26.25±0.59°) C, relative humidity (50.07±3.48)%, lighting time of 12 hours (07:00-19:00) was set and carried out. At this time, the experiment was divided into 7 groups of 9 animals for each group.

As shown in FIG. 14, the rest of the wrinkle-inducing group except for the normal group (N group) was irradiated with UVB irradiation step by step for weeks, and the UVB irradiation group was named as C group (control group). Groups to which 50 mg/kg, 150 mg/kg and 300 mg/kg of the mixed enzyme-treated extract samples of *Zizania latifolia* Turcz. prepared by the method of Preliminary Experiment 5 of the present invention were administered orally per body weight were named as Z50 group, Z150 group, Z300 group, and the group to which tricin, an indicator of *Zizania latifolia* Turcz., was administered orally at 0.3 mg/kg was named as T group and the skin application group of retinoic acid 0.05% was named as R group. At this time, oral administration or skin application of the sample was performed for 14 weeks, and in group R, 0.05% retinoic acid was applied to the skin 3 times a week by 50 ul by referring to the Brahim Chaqour method. For feed, solid feed for experimental animals (Samtaco BIOKOREA, Korea) was used, and drinking water was freely ingested. For 15 hours before dissection, only water was given and fasted. At this time, the experimental animals were treated within a certain time (10:00-12:00 in the morning) in consideration of the intraday changes in enzyme activity. This study was conducted in accordance with the policies and regulations of the Institutional Animal Care and Use committee of Southeast Medi-Chem Institute (SEMI) (Ethics Approval Number: SEMI-16-13).

The ultraviolet irradiation device (Dongseo Science, UV-1000) emits ultraviolet rays with a sunlamp that emits UVB in the cabinet, and the light source is 302 nm, and the UVB intensity is irradiated at a height of 0.3 mW/cm$^2$. Ultraviolet radiation dose was measured with a UV-radiometer, and after confining the mouse in a cage for ultraviolet irradiation, it was irradiated 3 times a week on the back area every other day, for a total of 10 weeks [0 week: 60 mJ/m$^2$ (1 M.E.D), 1 week: 120 mJ/m$^2$ (2 M.E.D), 2~3 weeks: 180 mJ/m$^2$ (3 M.E.D), 4~5 weeks: 240 mJ/m$^2$ (4 M.E.D) 5~10 weeks: 240 mJ/m$^2$ (4 M.E.D)].

First, the body weight of each animal was measured to observe the change in body weight.

To observe the appearance of wrinkles on the skin, after taking photos of the back surface of the experimental animal with a digital camera on week 5 to 14, and then a replica of the skin wrinkles on the same back was fabricated by using SILFLO (Flexico developments LTD. Tokyo, Japan) silicone rubber impression material and photographed under a microscope, and the patterns of wrinkles were compared and observed for each experimental group. In addition, the moisture level of the skin surface was checked to confirm the moisturizing effect closely related to the skin wrinkles.

More specifically, experimental animals whose breeding period has ended were fasted for 15 hours, anesthetized with $CO_2$ and opened, and blood was collected from the abdominal aorta using a 1 mL syringe. Aspartate aminotransferase (AST) and alanine aminotransferase (ALT) were tested in the serum obtained at this time. The specific experimental method was as follows:

Blood collected from the abdominal aorta was allowed to stand at room temperature for about 30 minutes, then centrifuged at 3,000 rpm for 15 minutes to obtain serum and used for serum biochemical analysis. The separated blood supernatant was used to analyze AST and ALT by serum biochemistry device (Rochu Ltd., Basel, Switzerland).

Skin and organs were extracted, washed with physiological saline, and then water was removed with filter paper and used for tissue staining and western blot experiments. In addition, the H&E staining experiment was carried out as follows: The cut skin tissue was put in 10% formalin to fix the tissue, washed with water, dehydrated sequentially with 60% to 100% alcohol, embedded in paraffin to prepare a block. The tissue sections with a thickness of 5 μm were obtained using a rotary microtome, stained with hematoxylin & eosin, and observed with an optical microscope (Nikon Co., Tokyo, Japan).

Next, the Masson's trichrome experiment was performed as follows: The cut skin tissue was fixed in 10% neutral formalin solution at room temperature for 24 hours, followed by washing with water, dehydration, transparency, and infiltration in a conventional manner, then embedded with paraffin to obtain a 4 μm-thick section and immersed in Bouin solution overnight at room temperature. After Mason's trichrome staining, the amount and shape of collagen fibers in the dermal layer were observed with an optical microscope.

Thereafter, the Western blot experiment of the skin tissue was performed as follows: For protein analysis, 20 mg of skin tissue was added to 200 μL of cell lysis buffer, the tissue was pulverized using a homogenizer, and then centrifuged at 800 rpm for 10 sec and only the supernatant was used. After 24 hours ice incubation, it was centrifuged at 14,000 rpm, 4° C., and 20 min. Thereafter, proteins were quantified using the Bradford assay, and separated by size using SDS-PAGE (polyacrylamide gel electrophoresis). After transferring to a PVDF (polyvinylidene fluoride) membrane using a semi-dry transfer system (Bio-Rad, USA), it was treated with a blocking buffer containing 5% skim milk (5% skim milk, 1× TBST buffer) for 1 hour. After washing for 10 minutes, 3 times with 1× TBST buffer, the primary antibodies were treated with collagen 1A, MMP-1, and MMP-13 (Santa-Cruz, USA) and reacted overnight at 4° C. for 10 minutes and washed with 1× TBST buffer for 10 minutes, 3 times. After reacting with the membrane using a Western Blot detection kit (Abfrontier, WEST SAVE GOLD, Korea), the expression level was observed using a Chemi-Doc (BIO-RAD XRS system, USA) equipment, and it was compared by calibrating with β-actin (SantaCruz, USA).

The results of the above experiments were statistically processed to calculate the mean value and standard deviation, and the significance test of each group was statistically analyzed using the Anova t-tes in Statview program.

2. Experiment Result

First, the weight change of SKH-1 mice in which wrinkles was induced for 10 weeks with a UVB irradiation device after oral administration of the *Zizania latifolia* Turcz. extract and tricin to each experimental group for 14 weeks was shown in FIG. 15. As a result, during the experiment, the body weight changes in the N, C and other sample treatment groups were all within the normal range.

As a result of checking the skin surface moisture, as shown in FIG. 16, in the group C, the moisture on the skin surface was markedly decreased, whereas the P group, the Z50 group, the Z150 group, the Z300 group and the T group, to which samples was administered for 14 weeks, were confirmed that the moisture of the skin surface was maintained.

As a result of serum AST and ALT test, as shown in FIG. 17, no significant difference occurred between groups despite administration of the sample for 14 weeks, and all were confirmed to fall within the normal range.

As a result of visual observation of the back surface, as shown in FIG. 18, it was observed that the skin surface of group C became dry, and the number of fine wrinkles gradually increased to thick wrinkles on the skin surface after an erythema response. On the other hand, on the back surface of the Z50 and Z150 groups administered with 50 mg/kg and 150 mg/kg of *Zizania latifolia* Turcz. for 10 weeks, erythema and keratin formation were significantly reduced than that of group C despite UVB irradiation, and it was confirmed that a small number of wrinkles were generated or maintained.

As a result of SILFLO microscopic observation, as shown in FIG. 19, group C had thick wrinkles, narrow gaps, and deep wrinkles, and Z50 and Z150 groups administered with 50 mg/kg and 150 mg/kg of *Zizania latifolia* Turcz. extract for 14 weeks, was confirmed that the wrinkles were relatively less formed or the thickness of the wrinkles was thin and the line thereof was thin, compared to group C. On the other hand, in group P to which 0.05% of retinoic acid was applied to the skin and group T to which tricin 2 mg/kg was administered, wrinkles were relatively less formed compared to group C until the 8th week of UVB irradiation, but by the 10th week of UVB irradiation, in group R, it was confirmed that the wrinkles became thicker and the number of wrinkles increased. In addition, in the group administered with 300 mg/kg of *Zizania latifolia* Turcz. extract (Z300 group), thick wrinkles were also observed under the SIL-FLO microscope, as in the previous observation of the back surface.

From the above, it is considered that the administration of 50 mg/kg and 150 mg/kg of *Zizania latifolia* Turcz. samples, despite the UVB irradiation for 10 weeks, will effectively act on the epidermal keratinocytes of SKH-1 hairless mice and help prevent skin wrinkles.

As a result of H&E staining, as shown in FIG. 20, in group C, the epithelial cell layer of the epidermis became very thick (marked by an arrow) by UVB treatment for 10 weeks, and drying was induced in both the epidermis and the dermal layer, and the elastic fiber layer was denatured. In contrast, it was confirmed that groups Z50 and Z150 treated with 50 mg/kg and 150 mg/kg of *Zizania latifolia* Turcz. for 14 weeks significantly decreased the epithelial cell layer compared to the group C. In addition, it was confirmed that the elastic fibers in the dermal layer became dense compared to the group C. This is consistent with the results of the morphological observations of the dorsal surface and the skin surface by SILFLO previously, and it can be seen that administration of a certain concentration of *Zizania latifolia* Turcz. extract has a positive effect on the epidermal layer and epithelial cells.

As a result of the Mason's trichrome staining, as shown in FIG. 21, collagen fibers strongly dyed in aniline blue were observed in the dermal layer of group N, but the collagen fibers of group C irradiated with UVB for 10 weeks were slightly dyed with aniline blue. On the other hand, as a result of administering the *Zizania latifolia* Turcz. extract for 14 weeks while irradiating with UVB, collagen fibers stained strongly in aniline blue were observed in the dermal layer of the *Zizania latifolia* Turcz. extract-administered group, especially, of the Z50 group, compared to group C. This is because the administration of *Zizania latifolia* Turcz. extract for 14 weeks (*Zizania latifolia* Turcz. 50 mg/kg, 150 mg/kg dose) maintained the collagen layer in the skin tissue despite excessive UVB irradiation for a long period of time, effectively blocked the formation of skin wrinkles and thus to keep compact the shape of collagen fibrous structure.

As a result of confirming the protein expression in the UVB irradiated skin tissue, as shown in FIG. 22, it was confirmed that the expression level of collagen 1A in the all groups administered with the *Zizania latifolia* Turcz. extract increased despite the UVB irradiation, compared to the group C. Particularly, it was confirmed that the Z150 group administered with 150 mg/kg of the *Zizania latifolia* Turcz. extract was found to increase the expression level of collagen 1A with a significance level of $p<0.001$. In addition, as a result of confirming the protein expression of MMP-1 and MMP-13, which are known as collagen-degrading enzymes, the expression levels of MMP-1 and MMP-13 increased in the UVB-irradiated C group, but the expression level of MMP-1 decreased in the Z50 group at $p<0.05$ significance level, and the expression level of MMP-13 also decreased at $p<0.05$ significance level in both Z50 and Z150 groups. On the other hand, in the R group, the expression levels of MMP-1 and 13 were significantly increased compared to the C group, and it was confirmed that applying retinoic acid three times a week did not affect the mechanism of collagen synthesis and degrading enzymes.

From the above results together, the expression of the collagen-degrading enzymes MMP-1 and MMP-13 protein increased and the expression of collagen 1A, a collagen synthase decreased due to excessive ultraviolet irradiation and it was found that the expression of collagen 1A increased and the expression of MMP-1 and MMP-13 was reduced due to the treatment with the *Zizania latifolia* Turcz. extracts (Z50 group, Z150 group) for 14 weeks, thereby helping to inhibit skin wrinkle formation.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A method of enhancing skin activities, comprising administering an effective amount of a cosmetic composition comprising an enzyme-treated *Zizania latifolia* Turcz. extract prepared by the method comprising the steps of:
   (1) adding water to *Zizania latifolia* Turcz. to produce a solution and heating for a sufficient duration of time;
   (2) cooling heated solution and treating with one or more enzyme(s) selected from the group consisting of: α-amylase, β-galactosidase, xylanase, lactase, lipase, tannase, cellulase, hemicellulase, pectinase and β-glucosidase, to produce an enzyme-treated solution;
   (3) filtering the enzyme-treated solution to obtain a primary extract and a remaining residue;
   (4) extracting the remaining residue after filtering in step (3) with any solvent selected from the group consisting of: water, lower alcohols of C1 to C4 and mixtures thereof to obtain a secondary extract; and
   (5) mixing the primary and secondary extracts and concentrating or drying to produce the enzyme-treated *Zizania latifolia* Turcz. extract;

wherein the enzyme-treated *Zizania latifolia* Turcz. extract contains 0.01% to 90% by weight of tricin.

2. The method of claim 1, wherein the skin activities are selected from the group consisting of skin whitening, moisturizing, anti-inflammatory, anti-allergy and anti-wrinkle.

3. A method of enhancing skin activities, comprising administering an effective amount of a health functional food comprising an enzyme-treated *Zizania latifolia* Turcz. extract prepared by the method comprising the steps of:
   (1) adding water to *Zizania latifolia* Turcz. to produce a solution and heating for a sufficient duration of time;
   (2) cooling heated solution and treating with one or more enzyme(s) selected from the group consisting of: α-amylase, β-galactosidase, xylanase, lactase, lipase, tannase, cellulase, hemicellulase, pectinase and β-glucosidase, to produce an enzyme-treated solution;
   (3) filtering the enzyme-treated solution to obtain a primary extract and a remaining residue;
   (4) extracting the remaining residue after filtering in step (3) with any solvent selected from the group consisting of: water, lower alcohols of C1 to C4 and mixtures thereof to obtain a secondary extract; and
   (5) mixing the primary and secondary extracts and concentrating or drying to produce the enzyme-treated *Zizania latifolia* Turcz. extract;

wherein the enzyme-treated *Zizania latifolia* Turcz. extract contains 0.01% to 90% by weight of tricin.

4. The method of claim 3, wherein the skin activities are selected from the group consisting of skin whitening, moisturizing, anti-inflammatory, anti-allergy and anti-wrinkle.

* * * * *